US010058476B2

(12) United States Patent
Baxter et al.

(10) Patent No.: US 10,058,476 B2
(45) Date of Patent: *Aug. 28, 2018

(54) DEVICES AND METHODS FOR INCREASED BLOOD FLOW AND PAIN CONTROL

(71) Applicant: MMJ LABS, LLC, Atlanta, GA (US)

(72) Inventors: Amy L. Baxter, Atlanta, GA (US); Louis A. Calderon, Atlanta, GA (US)

(73) Assignee: MMJ LABS, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/148,258

(22) Filed: May 6, 2016

(65) Prior Publication Data

US 2016/0354279 A1    Dec. 8, 2016

Related U.S. Application Data

(63) Continuation of application No. 13/795,683, filed on Mar. 12, 2013, now Pat. No. 9,333,144, which is a
(Continued)

(51) Int. Cl.
*A61B 19/00*  (2006.01)
*A61H 23/00*  (2006.01)
(Continued)

(52) U.S. Cl.
CPC ............ *A61H 23/00* (2013.01); *A61F 7/10* (2013.01); *A61M 5/422* (2013.01); *A61F 7/032* (2013.01);
(Continued)

(58) Field of Classification Search
CPC .. A61N 2/004; A61N 2/008; A61N 2005/002; A61N 2005/007; A61H 23/004;
(Continued)

(56) References Cited

U.S. PATENT DOCUMENTS 3,140,709 A     7/1964   Weisz et al.
3,620,209 A  *  11/1971  Kravitz ................. A61M 5/422
                                                            601/79
(Continued)

FOREIGN PATENT DOCUMENTS

AU     2007303111        10/2007
AU     2007303111 B2     10/2013
(Continued)

OTHER PUBLICATIONS

Lancet paper "Vibration Therapy for Pain," The Lancet, Jun. 20, 1992; 339(8808):1513-4.*
(Continued)

*Primary Examiner* — Ahmed Farah
(74) *Attorney, Agent, or Firm* — A. Ed H. Khalili; Bekiares Eliezer LLP

(57) ABSTRACT

A device comprising a casing; at least one vibratory source; at least one power source; at least one switch to actuate the vibratory source; electrical communication between the vibratory source, the power source, and the switch; and an optional thermal element for modulating the temperature of a contacted area of a surface. Also disclosed herein are methods for using the device.

19 Claims, 10 Drawing Sheets

Related U.S. Application Data continuation-in-part of application No. 13/426,330, filed on Mar. 21, 2012, now Pat. No. 8,740,960, which is a continuation of application No. 11/538,718, filed on Oct. 4, 2006, now Pat. No. 8,147,533.

(51) Int. Cl.

| | | |
|---|---|---|
| *A61M 5/42* | (2006.01) | |
| *A61F 7/10* | (2006.01) | |
| A61F 7/03 | (2006.01) | |
| A61F 7/00 | (2006.01) | |
| A61F 7/02 | (2006.01) | |

(52) U.S. Cl.
CPC ............... *A61F 2007/0001* (2013.01); *A61F 2007/0075* (2013.01); *A61F 2007/0078* (2013.01); *A61F 2007/0084* (2013.01); *A61F 2007/0285* (2013.01); *A61H 2201/0207* (2013.01); *A61H 2201/0214* (2013.01); *A61H 2209/00* (2013.01)

(58) Field of Classification Search
CPC .... A61H 2201/0221; A61H 2201/0214; A61H 39/00; A61H 39/007; A61F 7/02; A61F 7/10; A61F 2007/108; A61F 2007/023; A61F 2007/0228; A61F 2007/0282; A61F 2007/0285; A61F 2007/0295
USPC ............... 607/96, 108–112, 114; 601/46–48; 604/21, 22; 128/898
See application file for complete search history.

(56) References Cited

U.S. PATENT DOCUMENTS

| | | | |
|---|---|---|---|
| 4,082,918 | A | 4/1978 | Chang et al. |
| 5,148,804 | A | 9/1992 | Hill et al. |
| 5,179,944 | A | 1/1993 | McSymytz et al. |
| 5,289,438 | A | 2/1994 | Gall |
| 5,304,112 | A | 4/1994 | Mrklas et al. |
| 5,314,456 | A | 5/1994 | Cohen et al. |
| 5,327,886 | A | 7/1994 | Chiu et al. |
| 5,391,198 | A | 2/1995 | Cheney et al. |
| 5,447,531 | A | 9/1995 | Wood |
| 5,718,336 | A | 2/1998 | Haarlander et al. |
| 5,855,623 | A | 1/1999 | English et al. |
| 5,891,186 | A | 4/1999 | Daffer et al. |
| 6,023,932 | A | 2/2000 | Johnston |
| 6,187,031 | B1 | 2/2001 | Douglas et al. |
| 6,231,531 | B1 | 5/2001 | Zawadzki et al. |
| 6,234,986 | B1 | 5/2001 | Raffo et al. |
| 6,277,085 | B1 | 8/2001 | Flynn et al. |
| 6,554,787 | B1 * | 4/2003 | Griffin ............... A61F 7/02 601/70 |
| 6,641,522 | B2 | 11/2003 | August et al. |
| 7,693,580 | B2 | 4/2010 | Docherty et al. |
| 7,988,649 | B1 * | 8/2011 | Kost ............... A61H 23/02 601/15 |
| 8,147,533 | B2 * | 4/2012 | Baxter ............... A61F 7/10 128/898 |
| 8,740,960 | B2 * | 6/2014 | Baxter ............... A61F 7/10 128/898 |
| 9,333,144 | B2 * | 5/2016 | Baxter ............... A61H 23/00 |
| 9,358,152 | B2 | 6/2016 | Baxter et al. |
| 2001/0007952 | A1 | 7/2001 | Shimizu et al. |
| 2002/0058892 | A1 * | 5/2002 | Young ............... A61H 9/005 601/96 |
| 2003/0009168 | A1 | 1/2003 | Beale et al. |
| 2003/0015062 | A1 | 1/2003 | Sano et al. |
| 2003/0083599 | A1 * | 5/2003 | Kitov ............... A61H 23/0236 601/84 |
| 2006/0178715 | A1 | 8/2006 | Ahn et al. |
| 2006/0195168 | A1 | 8/2006 | Dunbar et al. |
| 2007/0100262 | A1 | 5/2007 | Simos et al. |
| 2007/0225618 | A1 * | 9/2007 | Ward ............... A61H 23/0236 601/2 |
| 2008/0086063 | A1 | 4/2008 | Baxter et al. |
| 2008/0255483 | A1 | 10/2008 | Goldberg et al. |
| 2009/0143689 | A1 | 6/2009 | Berry et al. |
| 2009/0151737 | A1 | 6/2009 | Baxter et al. |
| 2009/0176635 | A1 * | 7/2009 | Brinson ............... A61H 7/001 482/141 |
| 2010/0004570 | A1 * | 1/2010 | Torres Martin ........ A61H 7/005 601/17 |
| 2010/0004709 | A1 | 1/2010 | Mische et al. |
| 2012/0136287 | A1 * | 5/2012 | Barnard ............... A61H 19/44 601/46 |
| 2014/0163439 | A1 * | 6/2014 | Uryash ............... A61B 8/08 601/47 |

FOREIGN PATENT DOCUMENTS

| | | |
|---|---|---|
| CA | 2667629 | 10/2007 |
| CA | 2667629 A1 | 4/2008 |
| GB | 0907552.4 | 10/2007 |
| WO | 2006034324 A3 | 11/2006 |
| WO | 2006124329 A1 | 11/2006 |
| WO | 2008043051 A2 | 4/2008 |

OTHER PUBLICATIONS

Smith et al., "Vibration anesthesia: a noninvasive method of reducing discomfort prior to dermatologic procedures," Dermatology Online Journal, 2004, 10(2):1.*

Allsup et al.; Difficulties of recruitment for a randomized controlled trial involving influenza vaccination in healthy older people; Gerontology; 2002; 48(3):170-173.

Chen et al.; Topical anesthetics in children: agents and techniques that equally comfort patients, parents, and clinicians; Curr Opin Pediatr; 2001; 13(4):324-330.

Cohen et al.; Comparative study of distraction versus topical anesthesia for pediatric pain management during immunizations; Health Psychol; 1999; 18(6):591-598.

Cummings et al.; Prevalence and source of pain in pediatric inpatients; Pain; 1996; 68(1):25-31.

Eichenfield et al.; A clinical study to evaluate the efficacy of ELA-Max (4% liposomal lidocaine) as compared with eutectic mixture of . . . ; Pediatrics; 2002; 109(6):1093-1099.

Luhmann et al.; A comparison of buffered lidocaine versus ELA-Max before peripheral intravenous catheter insertions in children; Pediatrics; 2004; 113(3 Pt 1):217-220.

Palmon et al.; The effect of needle gauge and lidocaine pH on pain during intradermal injection; Anesth Analg; Feb. 1998; 86(2):379-381.

Ramsook et al.; Efficacy of ethyl chloride as a local anesthetic for venipuncture and intravenous cannula insertion in a pediatric . . . ; Pediatr Emerg Care; 2001; 17(5):341-343.

Saijo et al.; Lack of pain reduction by a vibrating local anesthetic attachment: a pilot study; Anesth Prog; 2005; 52(2):62-64.

Sinha et al.; Reducing venipuncture pain by cough trick; Anesth Analg; 2004; 99(3):952-953 (author reply 953).

Smith et al.; Vibration anesthesia: a noninvasive method of reducing discomfort prior to dermatologic procedures; Dermatology Online Journal; 2004; 10(2):1.

Spielberg et al.; Overcoming barriers to HIV testing: preferences for new strategies among clients of a needle exchange, . . . ; J Acquir Immune Defic Syndr; 2003; 32(3):318-327.

Taddio et al.; Effect of neonatal circumcision on pain response during subsequent routine vaccination; Lancet; 1997; 349(9052):599-603.

Wong et al.; Willingness to donate blood samples for genetic research: a survey from a community in Singapore; Clin Genet; 2004; 65(1):45-51.

"Vibration Therapy for Pain," The Lancet, Jun. 20, 1992; 339(8808):1513-4.

Search Report and Written Opinion for International Patent Application No. PCT/US2007/080497; dated Apr. 2, 2008.

(56) References Cited

OTHER PUBLICATIONS

Final Office Action issued by the USPTO dated Nov. 19, 2015 for U.S. Appl. No. 13/795,683, filed Mar. 12, 2013; Inventors, Baxter, et al.; 5-pgs.
Non-Final Office Action issued by the USPTO dated Mar. 27, 2015 for U.S. Appl. No. 13/795,683, filed Mar. 12, 2013; Inventors, Baxter, et al.; 7-pgs.
Final Office Action issued by the USPTO dated Jul. 24, 2013 for U.S. Appl. No. 13/426,330, filed Mar. 21, 2012; Inventors, Baxter, et al.; 5-pgs.
Non-Final Office Action issued by the USPTO dated Dec. 4, 2012 for U.S. Appl. No. 13/426,330, filed Mar. 21, 2012; Inventors, Baxter, et al.; 8-pgs.
Final Office Action issued by the USPTO dated Nov. 5, 2015 for U.S. Appl. No. 14/163,540, filed Jan. 24, 2014; Inventors, Baxter, et al.; 7-pgs.
Non-Final Office Action issued by the USPTO dated Mar. 27, 2015 for U.S. Appl. No. 14/163,540, filed Jan. 24, 2014; Inventors, Baxter, et al.; 6-pgs.
U.S. Appl. No. 11/538,718, filed Oct. 4, 2006, Baxter.
U.S. Appl. No. 11/867,630, filed Oct. 4, 2007, Baxter.
U.S. Appl. No. 12/371,206, filed Feb. 13, 2009, Baxter.
U.S. Appl. No. 13/426,330, filed Mar. 21, 2012, Baxter.
U.S. Appl. No. 13/795,683, filed Mar. 12, 2013, Baxter.
U.S. Appl. No. 14/163,540, filed Jan. 24, 2014, Baxter.
U.S. Appl. No. 14/874,909, filed Oct. 5, 2015, Baxter.
U.S. Appl. No. 15/148,258, filed May 3, 2016, Baxter.
PCT/US2007/080497 (WO 2008/043051), Oct. 4, 2007, Baxter (MMJ Labs LLC).

* cited by examiner

DEVICES AND METHODS FOR INCREASED BLOOD FLOW AND PAIN CONTROL

RELATED APPLICATIONS

This application is a continuation of U.S. patent application Ser. No. 13/795,683, filed Mar. 12, 2013, now U.S. Pat. No. 9,333,144, which is a continuation-in-part of U.S. patent application Ser. No. 13/426,330, filed Mar. 21, 2012, now U.S. Pat. No. 8,740,960, which is a continuation of U.S. patent application Ser. No. 11/538,718, filed Oct. 4, 2006, now U.S. Pat. No. 8,147,533, each of which is herein incorporated in its entirety.

TECHNICAL FIELD

The present invention generally relates to devices and methods for the improvement, of circulation, for example in blocked ducts, veins or arteries, and for pain control and irritating sensation control, such as itching and burning, by interfering with transmission of nerve signals by, for example, aDelta nerves, using devices capable of vibration and/or thermal effects.

BACKGROUND

Vibration has long been used to decrease the pain of dental injections, but vibrating needles have not been found to be effective in other dermal situations. Use of a simple hand-held vibrating massager has decreased injection pain in adults, and with the adjuvant of cold therapy was tested in both children and adults and found to relieve pain (Baxter et al. 2011; Baxter et al. 2009; Inal and Kelleci 2012).

Increasing vein diameter (vasodilation) is extremely important for venipuncture in children, as well as for circulation in adults. Venipuncture success in emergency department is regularly found to be between 55 and 65% (Taddio et al, 2005; Spandorfer et al. 2005) and can be as low as 49% in children (Hess 2010).

Devices in the prior art that have sought to induce vasodilation have used dramatically different means, including electrical stimulation and subsequent muscle contraction (US 2011/0071595), vacuum suction (U.S. Pat. No. 5,454,778), and compression (U.S. Pat. No. 6,129,688). Moreover, none of these devices are intended for increasing the success of venipuncture or reducing pain and discomfort associated with low blood flow.

Therefore, there is a need for an intentional agent (device and/or method) to increase vasodilation contributing to the success of venipuncture, improve blood flow for healing, and decrease claudication (pain from inadequate blood flow), which would include both vibration stimulation and a shape suitable to conform to the body. Such a device should be reusable, easy to clean, tolerable to children and adults, and should incorporate a method to be adapted for use in the developing world (for example, operation with a power cord, with a battery, with a solar or light cell, or without the need for external power). As ease of use is critical in this environment, embodiments that include rechargeable options, moveable locations, optional numbers of vibration units, or the option to include cold or heat also are contemplated.

Accordingly, there is a need for a device method that allows for the local improvement of blood flow, improvement of circulation in blocked ducts, veins or arteries, and for pain control and irritating sensation control. There also is a need for a device and method using vibration or a combination of vibration and thermal element that is applied to a subject prior to and/or during the provision of medications that create a burning or itching sensation when administered to a subject. It is to these needs and others that the present invention is directed.

SUMMARY

The present invention comprises methods and devices for increasing local blood flow and flow through ducts, veins or arteries, and for pain control and irritating sensation control, such as itching and burning, by interfering with transmission of nerve signals by, for example, aDelta nerves, using devices capable of vibration and/or thermal effects. A method of the present invention comprises contacting a device of the present invention near or at a site of restricted blood flow, for example, to small veins or a site of vasospasm, initiating vibration and/or thermal effects, for a time sufficient to effect an increase in the diameter of the blood vessels, such as veins or arteries, and reducing the blockage in ducts.

A method of the present invention comprises reducing the pain or irritating sensation, such as those caused by an injected medication, comprising contacting a device of the present invention between the spinal cord and the site where the pain or irritating sensation is initiated, such as a site of injection of a medication that causes a burning or painful sensation when injected; initiating vibration by the device in an intermittent or continuous vibration, optionally applying cold simultaneously with the vibration, vibrating for a sufficient time to interfere with nerve transmission as the injection is occurring, moving the device to the site of injection once the medication in injected, and initiating vibration at the injection site for a time sufficient to reduce the pain felt from the injection site optionally applying cold simultaneously to the injection site, to interfere with transmission of pain signals by aDelta nerves. The sensations from an injected medication, such as bunting or itching, are different from those produced by needle stick pain, and the burning and/or itching sensations are not found with all medications, whereas needle stick pain is generally found with all injections or needle sticks.

A method of the present invention comprises reducing an itching sensation in an animal, comprising contacting a device of the present invention to a site of itching, initiating vibration by the device, optionally applying a thermal effect simultaneously with the vibration, and reducing the sensation of itching, for example, by interfering with the transmission of nerve signals by aDelta nerves at the site of itching.

A method of the present invention comprises treating blocked mammary ducts, comprising, contacting a device of the present invention at or adjacent to a site of a blocked mammary duct, initiating vibration by the device, optionally providing a thermal effect simultaneously with the vibration, and modulating the condition of the blocked duct, for example, by at least releasing a portion of the blockage and/or relieving the pain caused by the blockage.

A device of the present invention comprises a casing, which may be shaped to conform to the contour of a surface, that contains a vibratory element, an optionally a thermal element. In an aspect, a casing or at least one surface of a casing, is shaped to fit a curved surface of the body. For example, one surface of a casing may be concave, shaped like the inner surface of a circle, and when the device contacts a surface, such as an arm, the concave surface of the casing substantially contacts the arm surface, meaning that a majority of the concave surface is in contact with the area of the surface. This contact of substantially the entire concave surface of the device allows for enhanced transfer of vibration and/or thermal effect to the surface. Vibration effects can be provided by any of the known vibratory devices such as, for illustrative purposes, a vibratory motor provided within the casing. Once vibration is initiated by providing power to the vibratory source, such as a vibratory motor, the vibration may be constant and continual, or the vibration may be intermittent, and cycle on and off at the same or a different vibration speed or frequency. Though not wishing to be bound by any particular theory, it is believed that intermittent vibration may aid in reducing or preventing habituation by the body to the vibrations.

An exemplary embodiment of the device comprises a casing housing the various components of the invention and an optional strap for holding the device to the subject. The casing may be manufactured of a stiff material to transmit vibration, and may be placed into a more flexible or pliant material in the form of a covering. The casing can be any shape, and preferably conforms to most body parts, particularly fingers, arms, and legs. For example, an application area may be concave or convex so conform to rounded areas of the body to which the device may be applied. Any other shape may be employed, so long as the shape is large enough and structured so as to be able to contain the various working components of the invention. A device of the present invention may optionally comprise an adhesive area on a portion or substantially all of the proximal side of an application area or a thermal element for affixing the proximal side of the casing/thermal element to a surface, such as the body or skin of a subject.

A method of the present invention comprises providing a device of the present invention externally to the skin surface of a subject. For example, the subject may be a human or animal to whom a hypodermic needle is being applied to either remove fluid from the subject or to inject a composition into the subject. The vibratory device of the present invention may be placed at a site of injection, pain, itching, bunting, blocked vessels, or may be placed proximal to such sites. In some methods, the vibratory device is placed at one site for a period of time and then moved to a second site. Methods of the present invention allow for increased blood flow, reduction of pain, reduction of irritating or unpleasant sensations, such as itching or burning, increased healing, or for blood drawing or injection procedures.

These features, and other features and advantages of the present invention will be apparent to those of ordinary skill in the relevant art when the following detailed description of the preferred embodiments is read in conjunction with the appended drawings in which like reference numerals represent like components throughout the several views. The figures and the detailed description which follow more particularly exemplify these and other embodiments of the invention.

BRIEF DESCRIPTION OF THE FIGURES

The accompanying Figures, which are incorporated in and constitute a part of this specification, illustrate several aspects and together with the description serve to explain the principles of the invention.

DETAILED DESCRIPTION

Figure 1:
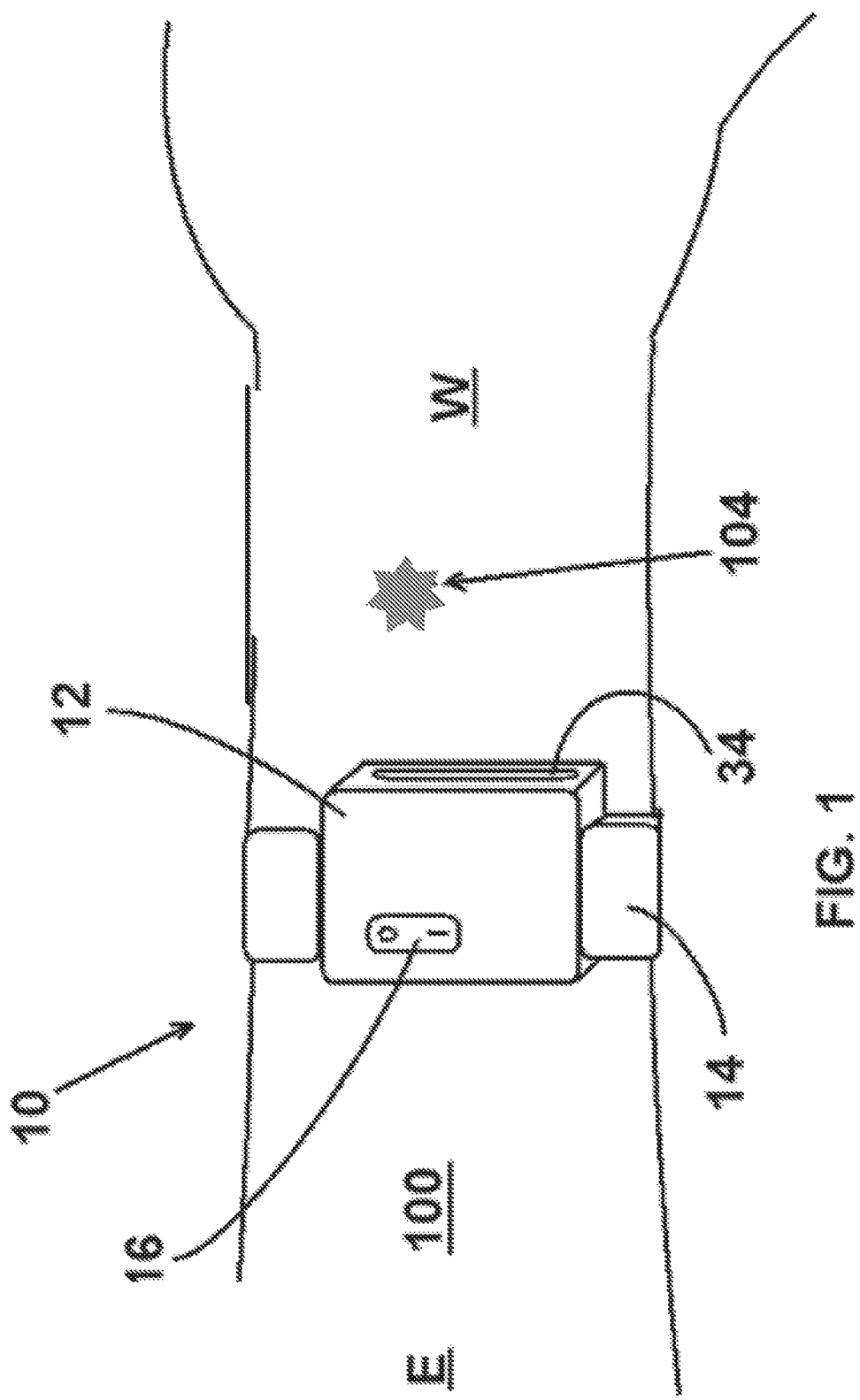
FIG. 1 is a perspective view of an embodiment of the invention. In the view, the device (10) is being applied to the arm (100) of a subject with an initiation site (104), which is a site of pain, or irritating sensation, such as burning or itching. The positioning of the device (10) on the subject is between the initiation site (104) and a nerve plexi (not shown, but the location of which is known to those of ordinary skill in the pain alleviation field) such as between the initiation site (104) and the proximal joint in this case the elbow (E). Thus, for the illustrated initiation site (104) on a subject's arm (100), the device (10) is placed closer to the elbow (E) than to the wrist (W) as this location puts the device (10) in between the initiation site (104) and the subject's brain. For example, the device 10 may be placed approximately 2.5 cm to 15 cm front initiation site (104).

The present invention comprises devices and methods for reducing pain or sensation, and for increasing blood or fluid flow in local areas. An embodiment of a device of the invention comprises a casing that contains a vibrational source, and an on/off switch for the vibrational source. A device may further comprise an attachment element for holding a thermal element in association with the casing. An attachment element (50) may be an integral portion of the casing, such as the clip shown in FIG. 9, or may be itself attached to the casing, such as the attachment element (50) shown in FIG. 7. An optional strap or wrap can be used to hold the device on to the subject, for example a strap that extends around a limb of the subject to secure the device on the limb of the subject such that the medical practitioner need not have an assistant present to hold the device, so that the medical practitioner can have both hands free to treat the subject, or a larger wrap that secures the vibratory device to a limb or body structure, for example, for an extended time. Further, a strap can act as a tourniquet, if necessary. Alternatively, the device can be held against the subject by the practitioner, the practitioner's assistant, or the subject.

A casing of a device of the present invention comprises an application area that comprises an optional thermal area and a vibrational area. The application area is the portion of the casing for contacting the surface or for contacting a thermal element that in turn contacts the surface. For simplicity of understanding, the surface may be referred to as the skin of a subject. In an aspect, the application area may be all or a portion of the proximal side of a vibratory device. A thermal element cooperates with the thermal area to apply cold or heat to the subject, and a vibrational source cooperates with the vibrational area to apply vibration to the subject. The placement of the thermal element is variable so long as the effects of the thermal element can be felt on the subject so as to produce thermal vasodilation or vasoconstriction. The placement of the vibrational source in the casing is variable so long as the vibrational effects of the vibrational source can be felt on the subject so as to produce vibrational vasodilation or is effective in stimulating nerves so that a pain or sensation message is blocked or interfered with in reaching the spinal cord nerves, and interfering with the perception of the pain or sensation by the subject. The walls of the casing define an interior space that, is sized to contain at least, the vibrational source, and a power source, such as batteries, and optionally a control element, a thermal element, a sound element, or a light element, and wiring to connect at least the vibrational source and the power source. An attachment element, a clip or hook on the proximal side (30), facing the subject surface, may be used to secure a thermal element to the device. An attachment element, such as an elastic band may also be used to secure the thermal element to the proximal side of a device of the present invention. Adhesive on the proximal side of the casing may be used to hold a thermal element to a device. A casing may further contain a control element for controlling the speed of vibration or period of vibration, for storing and providing sound, for providing a timing element, for controlling a light, such as turning a light, on or off, with or without, a timer, or making the light blink at a particular time point Devices and decorative casings, and the use of detractive media are disclosed in U.S. Pat. No. 8,147,533 filed Oct. 4, 2006, and issued Apr. 3, 2012, U.S. patent application Ser. No. 11/867,630, filed Oct. 4, 2007; Ser. No. 12/371,206, filed Feb. 13, 2009; and Ser. No. 13/426,330, filed Mar. 21, 2012, each of which is herein incorporated in its entirety.

A casing may further comprise on opening through a wall of the casing for providing an amplifier on the outer surface of the casing that is connected to a control element or a sound element contained within the casing. A casing may further comprise on opening through the casing for providing a light, such as an LED light, on the outer surface of the casing that is connected to a control element or a timing element contained within the casing. A light (and/or sound) may be turned on when vibration is initiated and turned off when power to the vibration element is turned off. Alternatively, powering on the vibration element may also power on a timing element, and optionally a light (and/or sound), so that when a desired time period has occurred, the timing element may turn off the light (and/or sound), or may turn off a light (and/or sound) and the vibration element, or the timing or control element may turn on sound or light after a period of vibration. Alternatively, the timing element may be under a control that is separate from a control for the vibration element. Components for switches, control elements, such as a polycarbonate circuit board and the programming to accomplish the disclosed activities and others, and elements such as timing elements, sound elements and lights, are known, and can be selected or commercially acquired by those of skill in the art. Wires for connecting the elements within the casing or on the surface are contemplated by the present invention.

Figure 7:
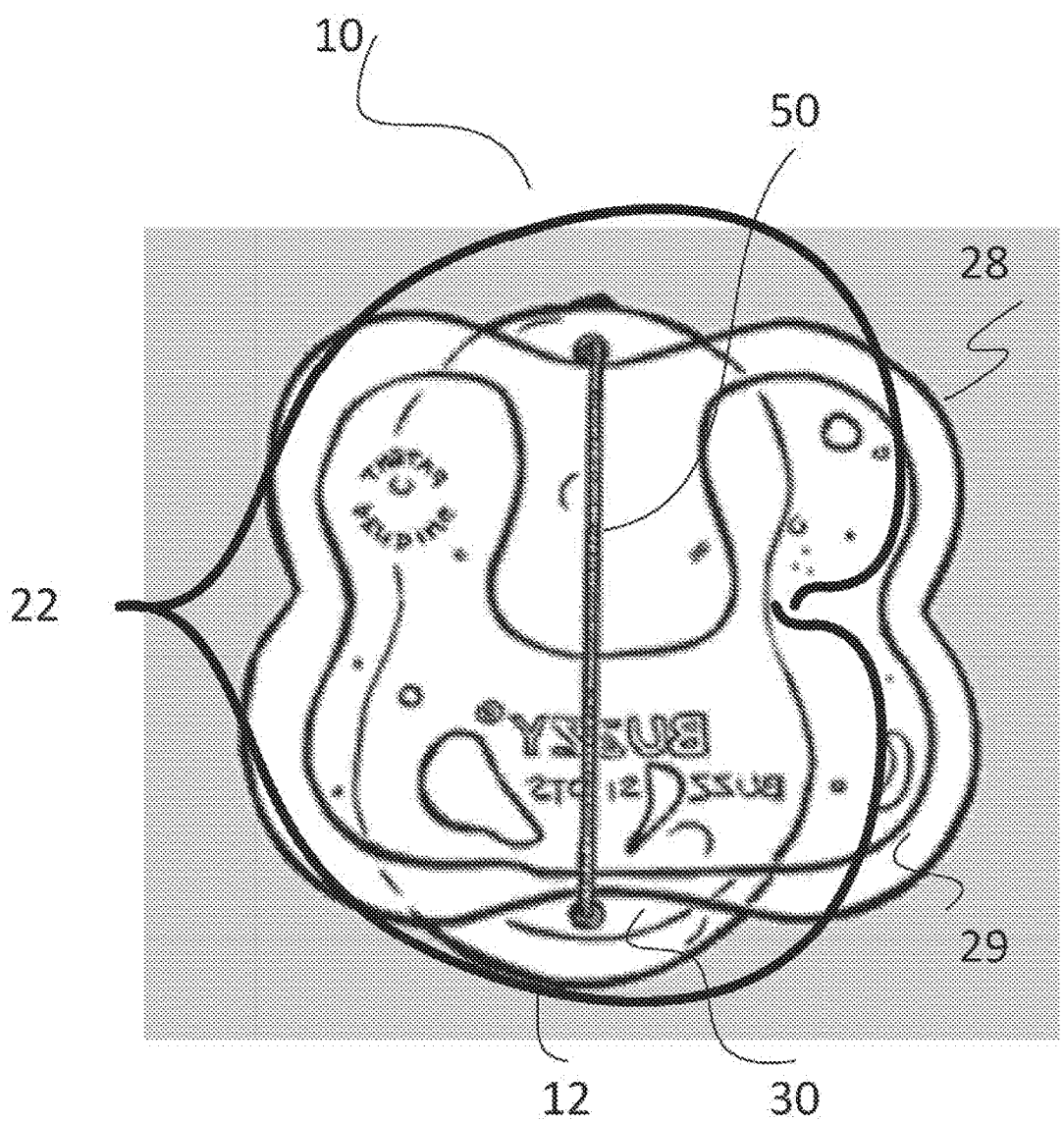
FIG. 7 is a drawing of the rear view of an exemplary device of the present invention showing the application area (22) of a device (10) comprising the proximal side (30) of the casing (12) and the proximal side (29) of a (transparent) thermal element (28) coextensive with the application area wherein thermal element (28) associated with the proximal side of casing (12) by use of an attachment element (50), which is an elastic band in this figure.
Figure 9:
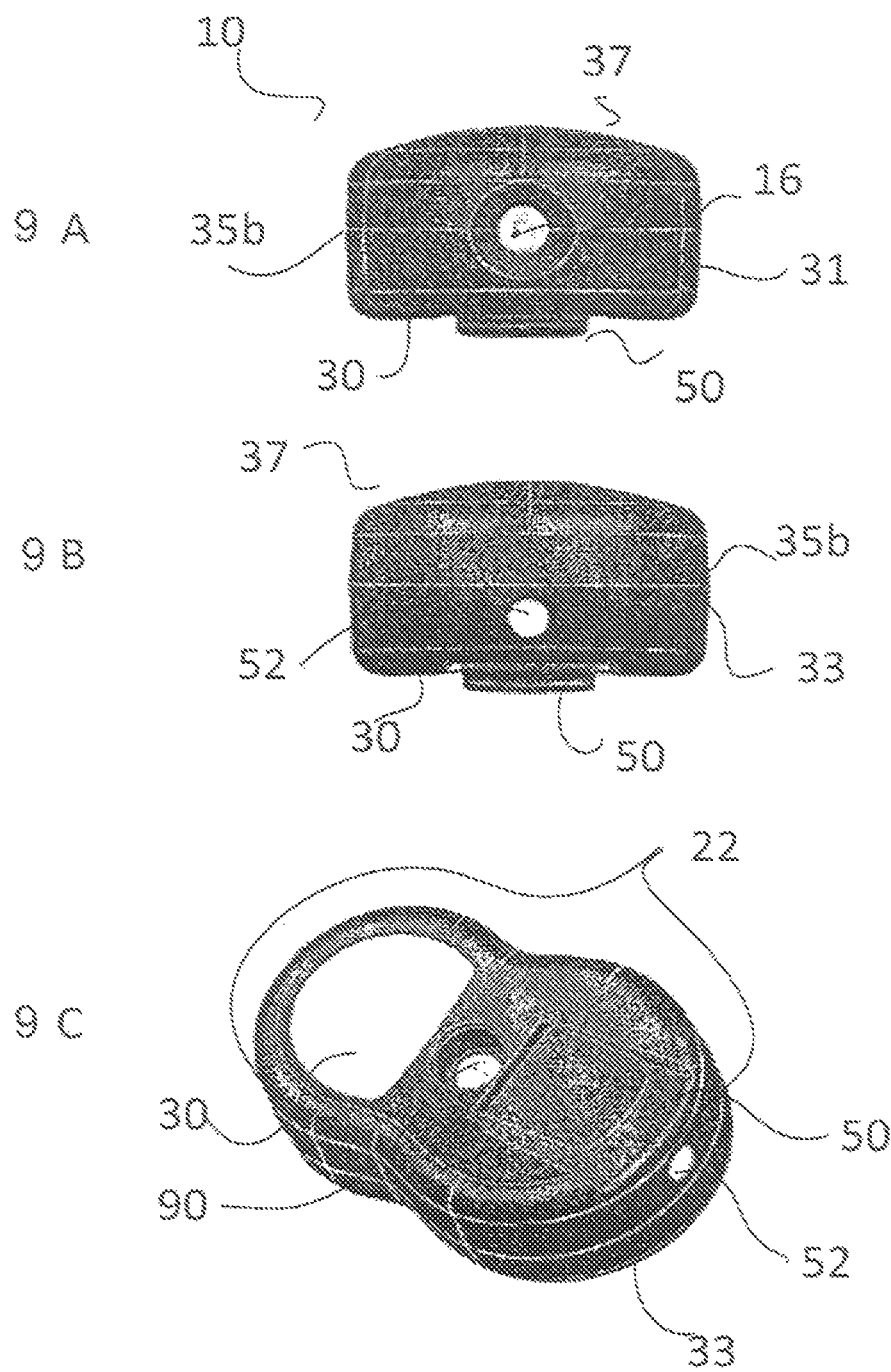
FIG. 9 A-E shows a drawing of an exemplary device of the present invention having a concave shaped casing. A shows the front or anterior end (31) of the device (10) and its power switch (16). B shows the posterior or rear end (3.3) of the device (10) with its site indicator (52), and C shows the back or proximal side (30) of the device, that is contacts, or is placed proximally or adjacent to, the surface, having a clip (50) for holding a thermal element (not shown) in place; D shows a front or distal side (37) of the device (10), and E shows a side view (35a or 35b) of the vibratory device (10) where the attachment element (50) a clip, slightly protrudes from the posterior (lower) (33) proximal end and the on/off switch element (16) is shown at the anterior (upper) end (31).
Figure 9:
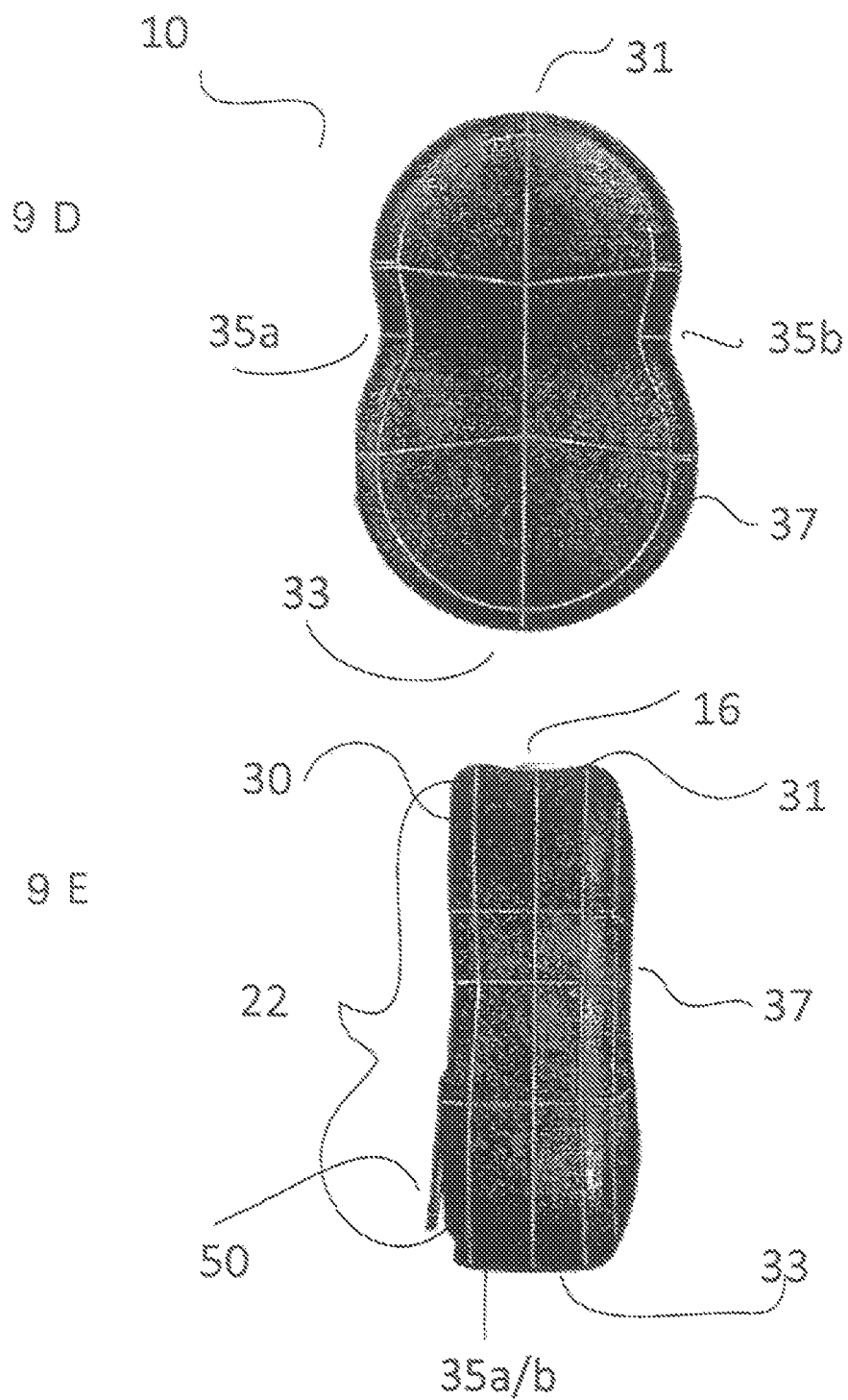

The casing may be shaped to provide an application area that is in contact with a surface so that substantially all of the application area contacts the surface. For example, a casing may be flat or concave in shape on at least its proximal side so that the application area is shaped so that substantially all of the proximal side of the casing contacts the surface of the surface. When a thermal element is placed on the proximal surface of the casing, substantially all of the proximal surface of the casing contacts the thermal element interposed between the casing outer surface and the contacted surface so that an area of the surface that is equivalent to the area of substantially all of the proximal side of the casing is contacted by the thermal element and receives vibrational effects therethrough (the application area). All or a portion of a casing may be curved. For example, the entire casing may be curved, such as in a concave direction (curved like the interior of a circle), so that the proximal side of the casing is contacting a surface through all or a portion of its surface (or the thermal element interposed therebetween) and the distal side (37) of the casing is curved to mirror the curve of the proximal side, so as to be comfortably held by a hand or held in place by a strap. Alternatively, only one surface, either the distal or proximal side may be curved, for example, where the proximal side is flat, but the distal side is curved. Additionally, a proximal side and/or a distal side of the casing may be flat or planar, and the lateral sides (35a or 35b) of the casing may be shaped, for example, as shown in FIGS. 7 and 9, there may be an indented area in the lateral sides. The lateral sides of the casing may be shaped in any form desired.

A casing may further comprise an adhesive area on a portion or substantially all of the application area. In an aspect, an adhesive area may be found on the proximal side of a thermal element and may cover a portion or substantially all of an area on the proximal side of the thermal element that corresponds to the application area of a device. A device of the present invention may optionally comprise an adhesive area on a portion or substantially all of the proximal side of the application area of the casing or the thermal element for attaching the proximal side of the device/thermal element to a surface, such as the body or skin of a subject. On the casing and/or thermal element, and before use, the adhesive area may be covered by a removable shield. In use, the removable shield is removed from the adhesive area on the proximal side of the casing and/or thermal element so that the adhesive is exposed and is capable of affixing the proximal side of a casing to a thermal element or to a surface, such as skin, or is capable of affixing the proximal side of a thermal element to a surface.

The vibrational source can be any conventional vibrational source or means for producing high frequency low amplitude vibrations. The on/off switch can be a common switch or a push button on/off switch, and is used to turn the vibrational source on and off. Once turned on, the vibrational source may vibrate in a constant and continuous mode, or the vibrations may be noncontinuous, such as intermittent periods or cycles of vibration and no vibration. The power source for operating the vibrational source can be any type of power source such as but not limited to a connection to an alternating current source (a wall plug), a solar or other light cell, a miniature reactor, a mechanical source such as a flywheel or springs, a disposable or rechargeable battery or the like.

In a method, a device of the present invention improves blood flow at least in the area contacted by the device, through the use of vibrational and/or thermal stimulation of blood and/or lymph vessels, or ducts of the body. In response to contacting the skin surface with a vibrating and/or thermal device of the present invention, blood flow in areas not specifically contacted by the device, such as blood flow in distal areas, may be improved, for example, in response to the increased blood flow at or near the site of contact. More specifically, the present invention comprises use of a device disclosed herein for concurrently applying a combination of vibrational effect and thermal effect to a surface area of a subject. In an aspect, the combined effects of vibration and thermal heat effects cause dilation of blood and/or lymph vessels proximal to the site of application of a device. In an aspect, the combined effects of vibration and thermal cold effects cause constriction of blood and/or lymph vessels proximal to the site of application of a device. In an aspect, for ducts of the body, for example, blocked mammary ducts, the combined effects of vibration and thermal heat effects cause a reduction in the transmission of pain signals from the blocked ducts, and also aid in reducing the blockage of the duct proximal to the site of application of a device. For example, the effects of vibration and/or thermal application may provide a local physiological effect to a surface and its underlying ducts or vessels within from 0.0 cm to 15 cm from the site of application of the device. Application of the device may have a more systemic effect by triggering a response in the local area, (0.0 cm to 15 cm) by a body part, such as a nerve, that has effects at a distant location, such as triggering a nerve response at the site of application that blocks nerve transmission of pain or sensation by spinal or other nerves. Local stimulation of blood, lymph or milk (or a body fluid in a duct) flow by a device of the present invention may alter blood, lymph, milk or duct fluid flow responses in vessels not in the area related to the surface contacted by a device of the present invention. It is known that vibration helps to reduce pain as the vibrational, or motion, nerves surmount the pain nerves, which is known as gate theory to those of ordinary skill in the field. Similarly, it is known that cold helps to reduce pain as the temperature nerves surmount the pain nerves. It also is known that warm thermal contact is effective at vasodilation. Stimulation of aDelta nerves, which is accomplished by a device of the present invention, may aid pain reduction, which may relax tenses muscles.

Though not wishing to be bound by any particular theory, it believed that vibrational effects may act to cause release of endogenous nitric oxide which increases lumen diameter. Use of a vibratory device of the present invention aids in the removal of blocked ducts, such as mammary ducts in breastfeeding females, blocked passages such those seen in pulmonary disease, for example, in subjects with cystic fibrosis, or arteries, veins and capillaries in tissues with blocked blood flow. A method of the present invention comprises treating a subject with cystic fibrosis to open blocked pulmonary ducts or passages, comprising contacting at least one site on the outer surface of the body overlying the lungs, bronchi or trachea with a device of the present invention, initiating vibration by device for a desired time period, optionally providing thermal effects from the presence of a thermal element interposed between the device application area and the contacted surface of the subject, optionally moving the device and providing vibratory and/or thermal effects to a second area of the subject, and affecting at least one pulmonary passage or duct of a subject. For example, in small human infants having blocked pulmonary passages such an infant with cystic fibrosis, a device of the present invention may have a flat proximal side for contacting at least a portion of the thoracic area of the infant, whether anteriorly or posteriorly or laterally on the subject, so that vibratory and/or thermal effects are provided to reduce blocked pulmonary passages and aid in unblocking clogged or blocked pulmonary passages. The gentle and directed vibrational and/or thermal effects for a controlled time period are beneficial for such blocked passages.

The present invention comprises methods comprising use of a device disclosed herein for increasing local blood flow. The present invention comprises methods comprising use of a device disclosed herein for increasing local lymph flow. The present invention comprises methods comprising use of a device disclosed herein for increasing local duct fluid flow. A method of the present invention comprises contacting a device of the present invention to a site of restricted fluid flow, for example, to a site of small arteries or veins, vessel spasm or vasospasm, or a site of blocked or restricted lymph or duct flow, initiating vibration and/or thermal effects, for a time sufficient to effect an increase in the diameter of the vessels, such as blood vessels, such as veins and/or arteries, lymph vessels, and ducts. For example, a device of the present invention is provided to an area of the breast where the duct is blocked. For example, the device, comprising the warm thermal element, is placed within bra cup containing the breast and is held in place next to the blocked duct area by the bra. The switch is activated so as to turn on the vibration element and the heat and vibrational effects are transmitted to the blocked duct area. This treatment causes reduction in pain from the blocked ducts, and reduces the duct blockage. The treatment may continue for several minutes at a time, wherein vibration and warmth are provided by the device to the blocked duct area, and such treatments may be repeated one or more times a day for one or more days. With repeated treatment, the extent of the blocked duct is reduced and the blockage may be resolved. With reduction in blockage, pain is also reduced, but the device also functions to block pain nerve transmissions during treatment.

A method of the present invention comprises reducing the pain or burning sensation caused by injected medication. Many medications, when injected, cause a bunting or painful sensation at the site of injection. This painful injection is disturbing to the subject receiving the injection and to the medical staff who provides the medication, and reduction of these side effects of injection would be beneficial for increased compliance by the subject and reduced stress for the medical staff. A method of reducing the pain or bunting sensation of an injected medication comprises a) contacting a device of the present invention with an area on the surface of a subject between the spinal cord and the site of injection of a medication, that causes a burning or painful sensation when injected, so that at least a portion of the application area of the device contacts the area; b) initiating vibration by the device in an intermittent or continuous vibration, and optionally applying a thermal effect simultaneously with the vibration; c) as the injection continues, so as to inject the medication solution, providing vibrating and/or thermal effect for a sufficient time to interfere with nerve transmission as the injection is occurring; d) once the medication solution is injected, moving the device to the site of injection; and e) continuing or initiating vibration and/or thermal effect at the injection site for a time sufficient to reduce the pain felt from the injection site. The thermal effect may cold or warm. The device may interfere with transmission of pain signals by aDelta nerves at the site of injection. For example, a subject is injected with a medication solution of Lovenox® (enaxaprin sodium) for deep vein thrombosis treatment or in conjunction with in vitro fertilization treatment, in a lateral abdominal area. This medication is known to cause pain or burning at injection. Immediately prior to injecting the needle into a pinched area of skin (subcutaneously), a device of the present invention comprising a cold thermal element is contacted with a first contact site which is the surface of the subject's skin anteriorly/laterally to the injection site, and within a 5-25 cm range from the site of injection. The device is switched on and continuous vibration and cold is provided to the contacted area. The Lovenox® solution is injected completely into the site. The device of the present invention is moved from its first contact site to the injection site and continuous vibration and cold is provided to the injection site. Alternatively, continuous vibration may be provided at the first contact site, and intermittent vibration provided at the injection site. Alternatively, intermittent vibration may be provided at the first contact site and at the injection site. The vibration is provided for a desired period, such as until the perception of pain is minimal. A medical provider or a user of the device can determine which type of vibration to use and how long to contact the device and/or the thermal element to the skin surface. Lidocaine also causes painful or irritating sensations (negative sensations) when injected, and injections of lidocaine may also be treated with a device of the present invention to relieve the painful and unpleasant sensations from providing the medication.

Methods of the present invention comprise reducing the negative sensations such as burning or itching caused by a medication injected into a subject, and such methods include medications that cause such sensations, not just those listed herein. For example, pharmaceutical or medical solutions infused into veins may cause pain to subjects receiving the solutions. Thought not wishing to be bound by any particular theory, it thought that the vibrational and/or thermal effects provided by a device of the present invention may block nerve transmissions from venous sensory nerves so that the burning and/or pain sensations from the infused medical or pharmaceutical solutions to the brain and/or spinal cord are blocked.

A method of the present invention comprises reducing an itching sensation in a subject, wherein the itching is localized to one or more areas. For example, the itching sensation may an acute reaction and be caused by an insect bite or an allergic reaction to contact with a substance or an injection which creates an irritated area of skin, or may be a chronic condition caused by constantly irritated nerves such as with dry skin, eczema or psoriasis, causing an irritated area of skin. A subject responds to itching by scratching, which may damage skin and lead to infection or permanent scarring of the skin. A method of the present invention comprises reducing scratching at a site of skin irritation, comprising a) contacting a device of the present invention with an irritated area of skin of a subject; b) initiating vibration by the device in an intermittent or continuous vibration, and optionally applying a thermal effect simultaneously with the vibration; c) continuing the vibration and/or thermal effect at the irritated skin site for a time sufficient to reduce the itching sensation felt from the irritated skin site. The thermal effect may cold or warm. The device may interfere with transmission of pain signals by aDelta nerves at the she of contact. The irritated skin is the source of the itching sensation. A method of the present invention comprises a method of reducing the itching sensation of a subject comprising, a) contacting a device of the present invention with an irritated area of skin of a subject; b) initiating vibration by the device in an intermittent or continuous vibration, and optionally applying a thermal effect simultaneously with the vibration; c) continuing the vibration and/or thermal effect at the irritated skin site for a time sufficient to reduce the itching sensation felt from the irritated skin site. The thermal effect may cold or warm. The device may interfere with transmission of pain signals by aDelta nerves at the site of the itching sensation. For example, a person has an area of skin that has eczema on her arm. A device of the present invention was kept by the bedside and when an itching sensation was triggered at the site of eczema of her arm in the night, instead of scratching the site and damaging the skin, the person contacted the device to the site of eczema on her arm, turned on the vibration effect for a period of 2 to 3 minutes. The device was then turned off, replaced on the bedside table, and the person returned to sleep. Use of the device prevented damage to the skin by scratching, and allowed for more restful sleep by the person.

A method of the present invention comprises treating pain from scrapes, such scrapes from falling on a rough surface, or from pain during medical cleaning or scraping of an open wound. When the structure of the skin is disturbed by a scrape, such as a rough abrasion of the skin due to a fall on a rough surface or rubbing against a surface such as in a motorcycle accident, many pain signals are sent to the brain. A method of interfering with transmission of pain signals caused by a scrape comprises a) contacting a device of the present invention with an area on the surface of a subject between the spinal cord and the site of the scrape, so that at least a portion of the application area of the device contacts the area; b) initiating vibration by the device in an intermittent or continuous vibration, and optionally applying a thermal effect simultaneously with the vibration, by interposing a thermal element between the application area of the device and the contacted surface; and c) providing vibrating and/or thermal effect for a sufficient time to interfere with nerve transmission to the brain, and to reduce the pain felt front the scrape site. The thermal effect may cold or warm. The device may interfere with transmission of pain signals by aDelta nerves at the site of the scrape. The device may be placed from 0.5 to 15 cm from the scrape site in a location that is between the scrape and the nerve plexus.

An open wound in the skin or underlying structures may be treated by medical personnel by scraping the wound with a blunt instrument to remove cellular debris or other debris present and this treatment is very painful, though necessary. A method of interfering with transmission of pain signals caused by a scraping treatment comprises a) contacting a device of the present invention with an area on the surface of a subject between the spinal cord and the site being treated by scraping, so that at least a portion of the application area of the device contacts the area; b) initiating vibration by the device in an intermittent or continuous vibration, and optionally applying a thermal effect simultaneously with the vibration, by interposing a thermal element between the application area of the device and the contacted surface; and c) continuing vibration and/or thermal effect at the site of for a time sufficient to reduce the pain felt from the site being scraped and treated. The thermal effect may cold or warm. The device may interfere with transmission of pain signals by aDelta nerves at the site of the wound or scraping treatment. The device may be placed from 0.5 to 15 cm from the scrape site in a location that is between the scrape and the nerve plexus.

A method of the present invention comprises treating neuropathic pain from nerve pain such as an outbreak of herpes simplex or shingles, or phantom pain from a missing limb. A method of interfering with transmission of neuropathic pain signals caused by viral infection such as cold sores or shingles, or from phantom limb pain, comprises a) contacting a device of the present invention with an area on the surface of a subject between the spinal cord and the site of nerve pain or in the case of missing limbs, between the spinal cord and the stump, or at the stump or terminus of the limb, so that at least a portion of the application area of the device contacts a portion of the surface area of the subject; b) initiating vibration by the device in an intermittent or continuous vibration, and optionally applying a thermal effect simultaneously with the vibration, by interposing a thermal element between the application area of the device and the contacted surface; and c) continuing vibration and/or thermal effect at the site of for a time sufficient to reduce the pain felt from the site. The thermal effect may cold or warm. The device may interfere with transmission of pain signals by aDelta nerves at the site. The device may be placed from 0.5 to 15 cm front the scrape site in a location that is between the scrape and the nerve plexus.

A burn site in the skin or underlying structures may be treated by medical personnel and burn treatment may be very painful, though necessary, and the healing period after a burn may be very painful even if no active treatment is made to the burn area. A method of interfering with transmission of pain signals caused by treatment of the burn or interfering with the transmission of pain signals from a burn when no active treatment is occurring comprises a) contacting a device of the present invention with an area on the surface of a subject between the spinal cord and the burn site, so that at least a portion of the application area of the device contacts the area; b) initiating vibration by the device in an intermittent or continuous vibration, and optionally applying a thermal effect simultaneously with the vibration, by interposing a thermal element between the application area of the device and the contacted surface; and c) continuing vibration and/or thermal effect at the site of for a time sufficient to reduce the pain felt from the burn site. The thermal effect may cold or warm. The device may interfere with transmission of pain signals by aDelta nerves at the burn site. The device may be placed from 0.5 to 15 cm from the burn site in a location that is between the burn and the nerve plexus.

Additionally, a burn site may have reduced blood flow into and/or out of the burn site. A method of increasing blood flow into and/or out of a burn site comprises a) contacting a device of the present invention with an area on the surface of a subject adjacent to the burn site, so that at least a portion of the application area of the device contacts the area; b) initiating vibration by the device in an intermittent or continuous vibration, and optionally applying a thermal effect simultaneously with the vibration, by interposing a thermal element between the application area of the device and the contacted surface; and c) continuing vibration and/or thermal effect at the site of for a time sufficient at least initiate increased blood flow into and/or out of the burn site. Multiple treatments of contacting an area adjacent to the burn site with a vibratory device of the present invention, optionally comprising a thermal element, may be desired to provide continued increased blood flow. The thermal effect may cold or warm. The device may provide vibratory effects including increasing blood or lymph flow. The device may be placed from 0.5 to 15 cm from the burn site.

The thermal element is cooled or heated, if necessary to within a predetermined temperature range. The thermal element may be placed within or attached to the casing. Alternatively, if the device is made to certain standards, the entire device already containing a thermal element can be cooled to the desired temperature. When a subject anticipates a need for a treatment using the device, the device is applied to the body at a desired location, such at the site to be treated or at a site proximate to a pain site and between the pain site and the brain and/or spinal cord, as described for treatments disclosed herein.

When a subject is to undergo a medical procedure, such as infusion of a medicinal solution that causes a burning or painful sensation, or scraping of a wound, or when deemed necessary by a subject, a device of the present invention comprising a thermal element may be applied to a selected area of the subject such that the vibrational area contacts the subject's skin through the thermal element to provide the application area. The optional thermal element may be allowed to act upon the subject for a time necessary to initiate thermal effects, which can be for a period of seconds up to a period of several minutes or more, or may be between 0 and 60 seconds. Once suitable thermal effects are achieved, or concurrently when the thermal element is applied to the subject, the vibrational source is actuated by the on/off switch, creating vibration. The vibrational source also is allowed to act upon the subject for a time necessary to initiate vibrational effects which can be for a period of seconds up to a period of several minutes or more, or may be from about 0 to about 60 seconds. If prolonged vibratory and/or thermal treatment is desired the device may be applied for a longer period to provide pain relief or relief from unpleasant sensations. Once the desired outcome is reached, the device may be removed from the subject, and/or the thermal element can be removed from acting on the subject and/or the vibrational source can be turned off. However, it is possible to leave the device, including the active thermal element and the active vibrational source in contact with the subject for prolonged periods of time. For example, the device may be left in place by using a wrap, and the device is then activated on an on-going schedule of time periods of use of the device and quiescence. One or more thermal elements may be provided to the device to allow for thermal effects to the subject during the periods of use.

"Thermal effects" as used herein includes, but is not limited to, the use or application of cold or reduced temperature (or the removal of heat) thermal elements or use of warm or heated thermal elements to a subject to induce a thermal effect, such as increased vascular diameter and increased arterial or venous blood flow, or constriction of vessels or inhibition of pain transmission "Vibrational effects" as used herein includes, but is not limited to, the use or application of vibration to a subject to induce vibrational responses in the subject, such as an increase in vascular diameter and increased blood flow from arteries, veins, or capillaries, or blocking of pain transmission by nerves, such as aDelta nerves, or blocking or reducing of burning, itching or other unpleasant sensation transmission to the brain and/or spinal cord.

"Vibrational and thermal effects" as used herein includes, but is not limit to the use or application of either heat or cold or reduced temperature (or the removal of heat) concurrently, substantially concurrently, or sequentially with the use or application of vibration to a subject to induce physiological changes in the subject in the area contacted by a device of the present invention or in a proximal or distal area.

Referring now to FIG. 1, a perspective view of an embodiment of the device is shown as applied to the arm of a subject, showing the casing that houses the various components of the invention and an optional strap for holding the device to the subject In the view, the device (10) is being applied to the surface (100) of a subject who has an initiation site (104), which is a site of pain or irritating sensation, such as burning or itching. As used herein, an initiation site is a site on a body that has reduced blood flow, reduced lymph flow, blocked ducts, is a site for painful sensations, a site of neuropathic pain, a site for unpleasant sensations including, but not limited to, itching and burning sensations, and those from insect stings, scrapes, or other abrasions to a body surface. For example, the initiation site may have reduced blood flow and contacting the initiation site with a vibrating and/or thermal effects providing device of the present invention may increase the blood flow or cause local vasodilation. For example, the initiation site may be a wound site, and contacting a site other than the initiation site, such as between the initiation site and the brain and/or spinal cord of a subject with a vibrating and/or thermal effects providing device of the present invention may reduce, impede or prevent transmissions of painful stimuli sensations to the brain.

The positioning of the device (10) on the subject is between the initiation site (104) and a nerve plexi (not shown, but the location of which is known to those of ordinary skill in the medical, field) such as between the initiation site (104) and the proximal joint, in this figure, an elbow (E). Thus, for the illustrated initiation site (104) on a subject's arm (100), the device (10) is placed closer to the elbow (E) than to the wrist (W) as this location puts the device (10) in between the initiation site (104) and the subject's brain. For example, the device 10 may be placed approximately 2.5 cm to 15 cm from initiation site (104). The on/off switch (16) is shown on the distal side of the device or casing, and a strap (14) is shown holding the device on the subject. A cuff, wrap, bandage or other similar component can be used in place of a strap to hold a device of the present invention on a subject.

The casing (12) may be manufactured of a flexible or pliant material such as for illustrative purposes a natural or synthetic woven or non-woven fabric, a rubber or other flexible polymer material, a silicone-based material, or may be a rigid material, such as a plastic, metal or wooden casing, wherein the casing is a container with walls to define an enclosed area. Other flexible or pliant or other materials may be employed, and it is preferred that the material of construction is non-toxic, hypo-allergenic and non-staining to the subject. A material that will transfer vibrations is contemplated by the present invention.

The casing can be any shape, and preferably is in the shape of a three-dimensional polygon (for use with an adult use) or an animal or other distractive shape (for use with a child) and the casing walls define a interior space or interior sections for containing the operating elements of the invention. Any other shape (as used herein, the term shape is used in the broad sense of three-dimensional works) may be employed, so long as the shape is large enough and structured so as to be able to contain the various working components of the invention as more fully disclosed below.

Figure 2:
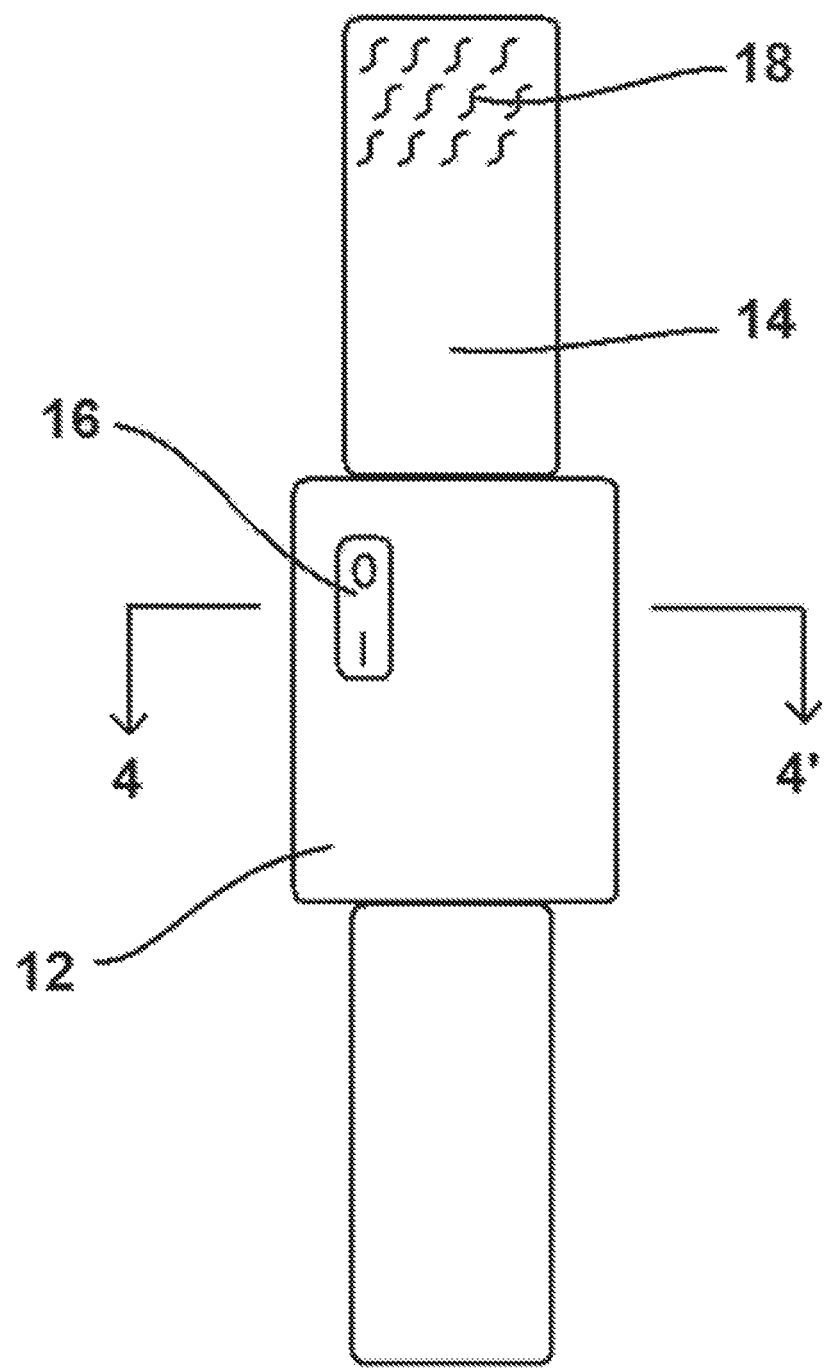
FIG. 2 is a top view of an embodiment of the invention with both vibration and cold capabilities. A minimal embodiment of the external features of the invention comprises the casing (12) and an on/off switch (16). Optional strap (14) can be used to hold the device on to the subject. Strap 14 can be attached to the casing (12) in any conventional manner or can be an extension of casing (12) itself. The ends of strap (14) preferably have some type of connecting device (18), such as a hook and loop fastener, a clasp, a clip, snaps, magnets, adhesive, or the like for attaching the device about the subject's body part. Alternatively, if the ends of strap (14) are flexible, the ends can be tied together around the subject's body part. The casing (12) of a device may be curved in a manner to enhance the attachment of the device by a strap or wrap.

The device is shown in FIG. 1 applied to the arm of a subject having an initiation site (104), which may be a painful site, such as a burn, a scrape and viral outbreak, or a site of medication infusion that is painful when infused, or may be a site of itching or other unpleasant and undesired sensation. The positioning of the device on the subject may be between the initiation site (104) and a nerve plexi (not shown, but the location of which is known to those of ordinary skill in the medical field) or between initiation site (104) and the spinal cord or brain. In this example, the device is placed at or proximal to the elbow E. Preferably, the device is placed approximately 2.5 cm to 15 cm from the initiation site (104). A thermal element pocket (34) in the easing is illustrated on this embodiment. An embodiment showing the distal side of the invention of FIG. 1 is shown in FIG. 2, comprising the casing (12) and an on/off switch (16). An optional strap (14) can be used to hold the device on to the subject. Alternatively, the device can be held against the subject by medical personnel, or the subject. The strap (14) can be attached to the casing (12) in any conventional manner or can be an extension of casing itself. For example, the strap and casing can be attached together much like a conventional watch and watchband with hinges or pins. Or in another embodiment, the strap can be an extension of the fabric or other material enclosing the casing, such as an extension of a decorative cover (shown in FIG. 6). The ends of strap preferably have some type of connection element (18), such as a hook and loop fastener, adhesive, a clasp, a clip, snaps, magnets, or the like for attaching the device about the subject's body pan. Alternatively, if the ends of the strap are flexible, the ends can be tied together around the subject's body part.

Figure 3:
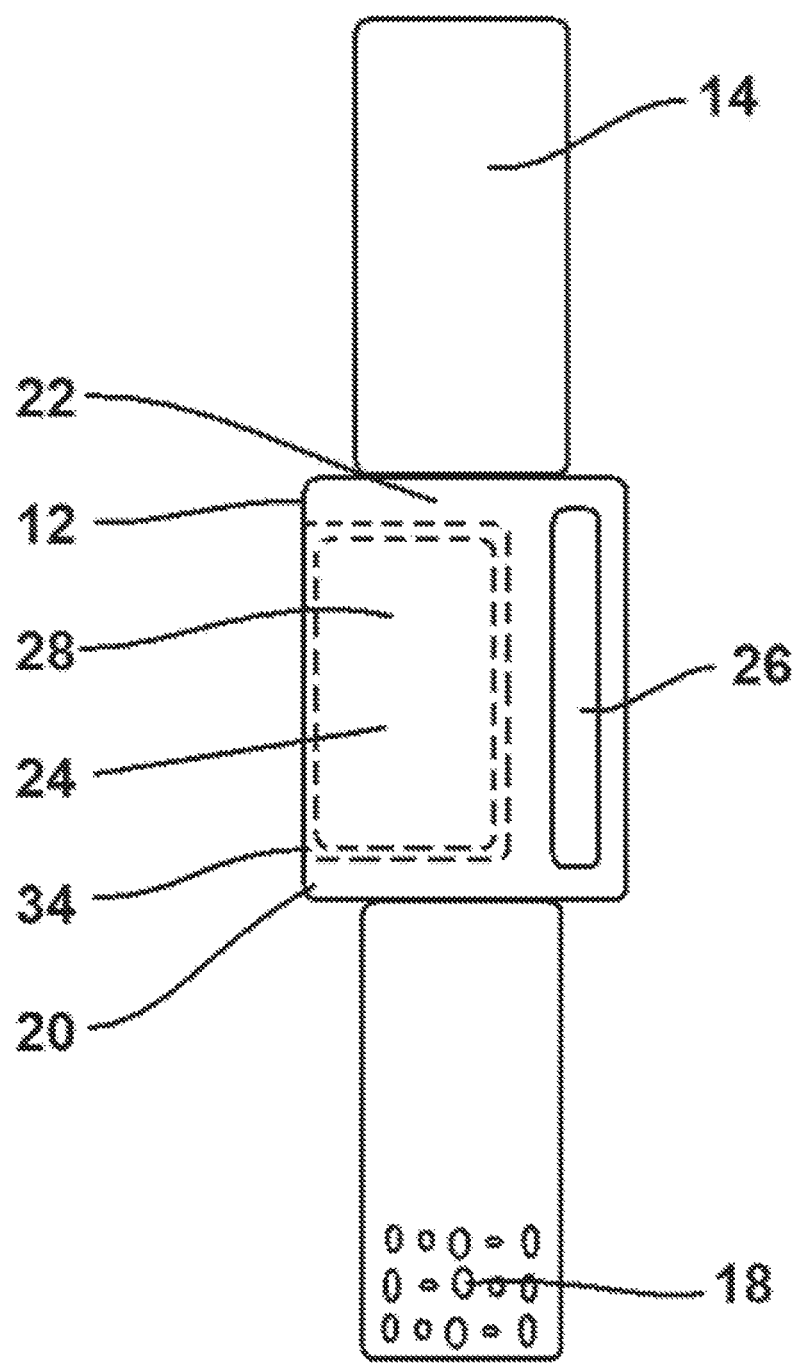
FIG. 3 is a bottom view of an embodiment of the invention with both vibration and cold capabilities. The casing (12) has a peripheral bottom rim (20) that defines an application area generally designated (22). Application area (22) comprises thermal area (24) and vibration area (26). Although thermal area (24) and vibration area (26) area shown as discrete areas, this is for illustrative purposes only, as there need not be any physical delineation between thermal area (24), vibration area (26), and application area (22) and these areas can overlap and be coexistent as the same area, which may be referred to as application area (22). Thermal element (28) cooperates with thermal area (24) to apply cold or heat to the subject, and vibrational source (32) (not shown) cooperates with vibration area (26) to apply vibration to the subject. Thermal area (24) and vibrational area (26) can occupy the same area, and form application area (22). Thermal element (28) may be located within thermal element pocket (34).

Referring now to FIG. 3, a bottom or proximal view of an embodiment of the invention of FIG. 1 is shown. The casing (12) has a peripheral bottom rim that defines an application area (22). Application area (22) comprises thermal area (24) and vibration area (26). Although thermal area (24) and vibration area (26) area shown as discrete areas, this is for illustrative purposes only, as there need not be any physical delineation between thermal area (24), vibration area (26), and application area (22) and these areas can overlap and be coexistent as the same area, which may be referred to as application area (22). Thermal element (28) cooperates with thermal area (24) to apply cold or heat to the subject, and vibrational source (32) (not shown) cooperates with vibration area (26) to apply vibration to the subject. Thermal area (24) and vibrational area (26) can occupy the same area, can coextend and form application area (22). Thermal element (28) may be located within thermal element pocket (34). The thermal pocket (34) is a slot, fold or other type of compartment in the casing into which the thermal element can be placed. As shown in FIG. 3, the thermal element pocket is accessed on the side of the casing via a mouth or an opening in the casing. Alternatively, the opening for the pocket can be located at other sites on the casing depending on the size and shape of casing and the location of the vibrational source within the casing. Alternatively, the thermal element can be contained within the main housing volume of the casing. Thus, the placement of the thermal element is variable so long as Die cooling or heating effects of the thermal element can be felt on the subject so as to produce thermal effects. Thermal area in its simplest form is an area on the application area on the device that allows the thermal effects from thermal element to contact the subject.

The vibration area is an area on the casing in vibratory contact with the vibrational source. As disclosed in more detail below, vibrational source preferably Is contained within the main housing volume of the casing. The placement of the vibrational source is variable so long as the vibration effects of vibrational source can be felt on the subject so as to produce vibrational effects. As shown in FIG. 3, vibrational area is proximal to thermal area; however, vibrational area can coextend with thermal area. Vibrational area in its simplest form is an area on the application area on the device that allows the vibrations from vibrational source to contact the subject.

Figure 4:
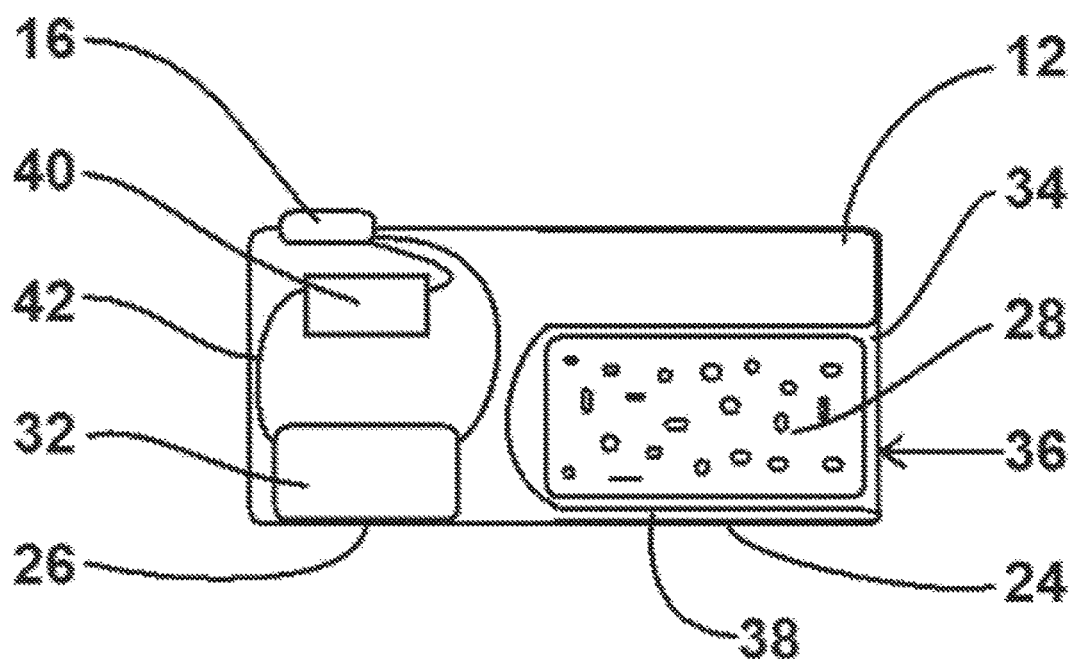
FIG. 4 is sectional side view of the embodiment of the invention as shown along the latitudinal line 4-4' of FIG. 2. The casing (12) is a generally hollow structure sized to contain a thermal element (28) and a vibrational source (32). Thermal element (28) can be placed within thermal element pocket through mouth or opening (36) and can be held within thermal element pocket (34) by friction, adhesives, fasteners, or by a zipper or other type of closure on mouth or opening (36). It is preferable that the bottom wall (38) of thermal element pocket (34) be sufficiently thin or having sufficient thermal transfer characteristics so as to allow the efficient transfer of cold or heat from thermal element (28) to the subject. The vibrational source (32) further comprises a power source (40) and wiring (42) electrically connecting vibrational source (32) and power source (40) to on/off switch (16).

Referring now to FIG. 4, a sectional side view of the embodiment of the invention as shown along line 4-4' of FIG. 2 is shown. The casing (12) is a generally hollow structure sized to contain an optional a thermal element, and a vibrational source. A casing (12) can be a rigid hollow container having an interior volume or a flexible or pliant container having an interior volume. Such containers are known, as well as their materials and methods of construction are within the skill of those in the art. The casing may be constructed such that casing (12) can contain and hold a vibrational source, and optionally, a thermal source, in a predetermined position relative to the subject when the device is contacting a subject.

As shown illustratively in FIG. 4, thermal element is contained in thermal element pocket. Thermal element can be placed within thermal element pocket through mouth or opening and can be held within thermal element pocket by friction, adhesives, fasteners, or by a zipper or other type of closure on the pocket mouth or opening. It may be desired that the bottom wall of thermal element pocket be sufficiently thin or have sufficient thermal transfer characteristics so as to allow the efficient transfer of cold or heat from thermal element to the subject. Alternatively, a thermal element (28) may be placed on the outside surface of the proximal side of a casing so that in use, the thermal element is interposed between the proximal surface of the casing and the subject's surface.

Thermal element can be any conventional thermal element capable of storing and transferring cold (removing heat). Illustrative examples of suitable thermal elements include metal ingots, low freezing point (below about 45° F. or 7.2° C.) liquids and gels, ceramics, polymers, polymer materials, natural materials such as bran, other heat sinks, hot packs, chemical reactive thermal packs, thermal gel packs, and even ice packs. Such thermal elements are known. It is only important that thermal element is able to transfer cold or heat to the subject in a sufficient amount so as to produce the desired effect, for example vasodilation, pain reduction, itching sensation reduction, or reduction in blocked vessels. For example, providing a temperature of below about 45° F. or 7.2° C. and between about 28° F. or −2.2° C. and about 54° F. or 12.2° C. or between about 38° F. or 3.3° C. and about 45° F. or 7.2° C., or for example about 34° F. to the subject prior to and during the treatment method is sufficient to provide a suitable level of effective thermal treatment. The thermal element is applied to the subject for a time period sufficient to initiate treatment, such as thermal vasodilation, which can be between 0 seconds and several minutes or more depending on the subject. For example, in some applications, it is desirable to apply the thermal element to the subject for a period of about 0 to 60 seconds, or longer, prior to initiating an activity, such as injecting a medication that causes a painful or burning sensation, or scraping of a wound, and continuing the application of the thermal effect and/or vibration during the activity to provide a suitable level of effective treatment, by the device.

The thermal element may be any conventional thermal element capable of storing and transferring heat or cold. Illustrative examples of suitable thermal elements include high specific-heat capacity material like grains, such as wheat or buck wheat, sewn within an insulated fabric such as flannel, chemical thermal elements like calcium chloride- or supersaturated sodium acetate-based heat pads, or other conventional heat/cold packs. A thermal element may be a gel or other type of heat/cold pack that may be placed in a freezer or microwave and such heat/cold packs are known in the art. The present invention contemplates use of thermal elements that are known in the art. The thermal element needs to transfer heat or cold to the subject in a sufficient amount so as to produce the desired effect of such heat or cold, for example vasoconstriction or vasodilation. One of skill in the art, such as medical personnel, or a subject, can determine an adequate temperature and time for application of the thermal element for methods disclosed herein. The thermal element is applied to the subject for a time period sufficient to cause the desired effect, which can be between 0 seconds and several minutes or more depending on the subject and/or the method. A second or third thermal element may be used in replacing a first thermal element used in a method, especially in methods where application of vibration and/or thermal effects continue for a longer time period than the first thermal element can maintain the desired temperature.

As shown illustratively in FIG. 4, the vibrational source (32) is contained within the interior of the casing (12). Vibrational source (32) can be placed within casing (12) during manufacture or at any time after manufacture. An ingress and egress element (90) is preferred, as one embodiment of vibrational source utilizes a battery as the power source, and it may be accessory to change the battery on occasion. See FIG. 9C where an ingress/egress element (90), as illustrated, is a screw, is shown for opening the casing (12), and may be used for holding a control board, and/or power source and/or vibrational source (motor), or other components on a control board in the interior of the casing (12). Ingress/egress element (90) can be a snap, a screw, a bolt, or any closure components that would releasably hold the casing closed and allow for access to at least a power source within the casing. Vibrational source (32) and power source (40) can be held within casing by friction, adhesives, fasteners, or other types of securing means. Alternatively, the interior volume of casing can be approximately the same dimensions as the vibrational source, including the power source, such that additional means for securing the vibrational source 28 are unnecessary. In an aspects, the proximal side (30) of the casing which is adjacent to vibrational source be sufficiently thin or have sufficient vibrational transfer characteristics so as to allow the efficient transfer of vibration from vibrational source to the application area (22) of the casing (12) and thus to the subject to be treated in the methods disclosed herein.

Vibrational source (32) can be any conventional vibrational source or means for producing vibrations. As shown in FIG. 4, vibrational source further comprises a power source (40) and wiring electrically connecting vibrational source find power source to an on/off switch. Illustrative examples of suitable vibrational sources include elliptical flywheel motors, eccentric motors, and the like. Such vibrational sources are known. It is only important that the vibrational source be able to transfer vibration to the subject at a sufficient level to produce the effect intended in the disclosed methods. For example, a device of the present invention can provide vibrations of between about 175-250 Hz. The application area of the device which vibrates due to the action of the vibrational source is applied to the subject for a time period sufficient to accomplish the effect intended in the disclosed methods, which can be between 0 seconds and several minutes or more depending on the subject and/or the method. For example, the application area of the casing may provide vibration to the subject for a period of about 0 seconds to about 60 seconds, or longer in certain methods, to accomplish the effect intended in the disclosed methods. A vibrational source may be a high frequency low amplitude eccentric motor. The motor may be controlled by a logic control board, such as a polycarbonate board, which known in the art. The motor and/or a power source may be held to a board by brackets, screws or other known attachment elements.

A vibrational source can produce a single vibrational cycle, multiple vibrational cycles, or be variable, for example in the vibrations per minute in a particular cycle, or in the number of vibrational cycles. In other words, the vibrational source can be a vibrational motor that operates at, for example, 4700 vibrations per minute or, for another example, at 5700 vibrations per minute, or in a range from about 6,000 to about 15,000 vibrations per minute, or from about 8,000 to about 14,000 vibrations per minute, or from about 9,000 to about 13,000 vibrations per minute, or any vibrations per minute thereinbetween. Alternatively, vibrational source can be a vibrational motor that operates at two or more vibrational cycles, for example, 9,000 vibrations per minute and 13,000 vibrations per minute, and can be switched between vibrational cycles by a switch or other control element. Alternatively, vibrational source can be a vibrational motor that operates at many different vibrational cycles along a continuum by using a potentiostatic switch, for example, vibrational source can be varied continuously or step-wise between 3000 vibrations per minute and 15,000 vibrations per minute. In an aspect, the vibrational source may provide intermittent vibration cycles, which may be the same or different vibrations per minute. For example, a vibrational source may provide 10,000 vibrations a minute for 4 seconds, stop vibrating for 4 seconds, thus completing one cycle of vibrations, then provide another cycle of vibrations at 10,000 vibrations a minute for 4 seconds, stop vibrating for 4 seconds, and so on. The vibrations per minute may remain the same for each cycle, or may vary randomly or vary in an increasing or decreasing manner. The time of vibration may vary randomly for each cycle, or may vary in an increasing or decreasing manner. The time of no vibration may vary randomly for each cycle, or may vary in an increasing or decreasing manner.

A switch may be a common Switch and is used to turn the vibrational source on and off, namely to start and stop the vibration, respectively. The switch may also control power transmission to a control element or other element of the device, such as a sound element or a light. The switch can be secured to the casing at any convenient position where it may readily be actuated, or accessed remotely by wired or wireless components. As shown in FIG. 9, the switch is located at the anterior side (31) of the device and is a push button switch. The switch is electrically connected in a known manner between the power source and the vibrational source to control the application of power to the vibrational source. In an aspect, when the vibrational source is switched on, the vibrating force produced from the vibrational source, such as the various types of motors disclosed above, will be transmitted through the casing to the contacted surface.

A device of the present invention may have more than one switch, each of which may control the power to an element of the device, or provide on/off control of the element itself, and discussion of one switch is not to be seen as limiting to the invention. A switch can be a common on/off switch, such as a toggle, lever, push-button, capacitance or other switch. This type of switch would be practical with a single vibrational cycle motor. Alternatively, switch can be a common three-way switch. This type of switch would be practical with, a double vibrational cycle motor. Alternatively, a switch can be a common potentiostat. This type of switch would be practical with a vibrational motor that operates at many different vibrational cycles along a continuum. The selection of the type of switch and the control element of a device is within the skill of those knowledgeable in the art. For example, a switch can turn power on or off to a control panel that in turn controls a vibration source, and/or other elements of the device, such as sound or light elements.

Figure 5:
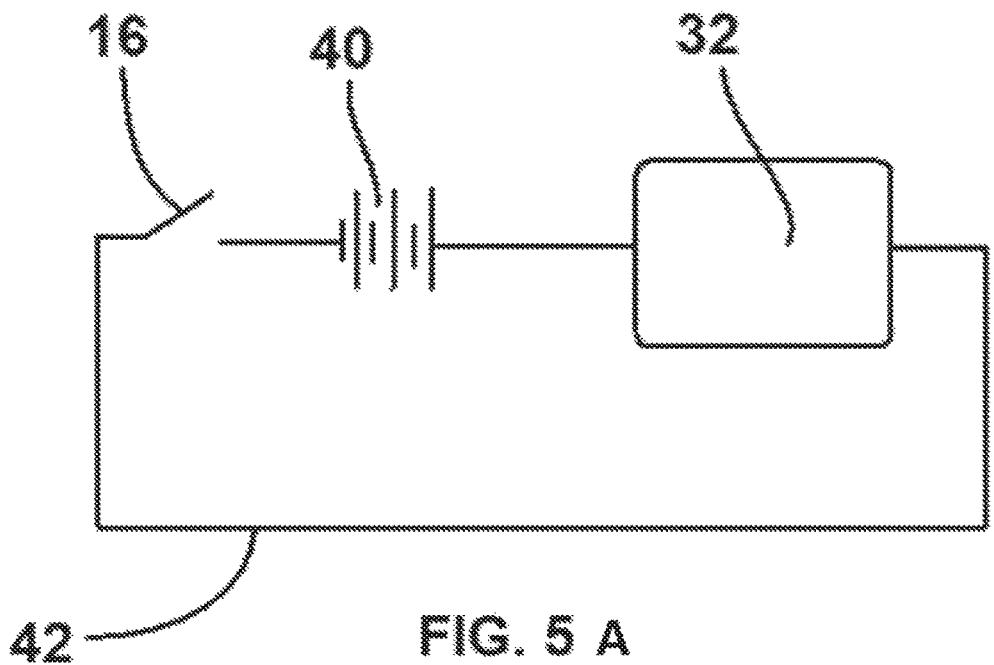
FIG. 5A is a circuit diagram of an embodiment of the invention. A representative circuit diagram for the vibrational source (32) is shown. The vibrational source (32), power source (40), and on/off switch (16) are electrically connected in series by wiring (42).
FIG. 5B is a circuit diagram of an embodiment of the present invention comprising a vibrational source (32), a push button on/off switch (16), a battery power source (40), a control board (45), and optionally a speaker (46) and a fight (47), in electrical connection in series by wiring (42).
Figure 5B:
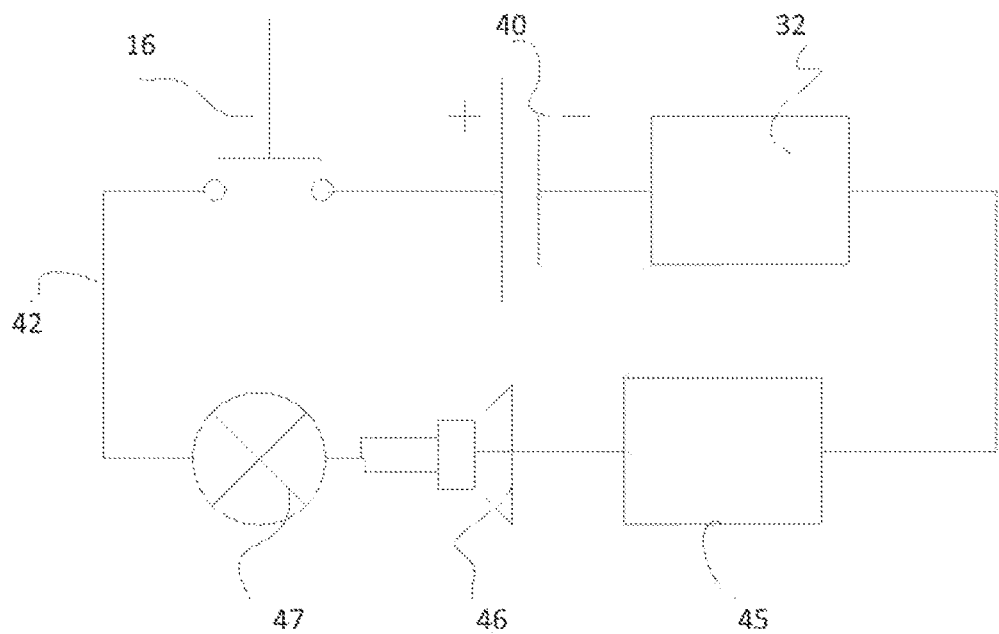

Referring now to FIG. 5A, a representative circuit diagram for the vibrational source is shown. Vibrational source, power source and on/off switch, are electrically connected in series by wiring. Power source is illustrated in FIG. 5 as a battery; however, power source can be any type of power sources such as but not limited to a connection to an alternating current source (a wall plug), a solar or other light cell, a reactor, a mechanical source such as a flywheel or springs, or the like. It is only important that power source be able to provide sufficient power to vibrational source so as to produce sufficient vibration for effecting vibrational vasodilation. FIG. 5B is a circuit diagram of an embodiment of the present invention comprising a vibrational source (32), a push button on/off switch (16), a battery power source (40), a control board (45), and optionally a speaker (46) and a light (47), in electrical connection in series by wiring (42).

In operation and use, a device of the present invention is effective in achieving the methods disclosed herein. According to known gate theory, vibration helps to reduce pain as the vibrational or motion nerves surmount the pain nerves. Similarly, it is known that cold helps to reduce pain as the temperature nerves surmount the pain nerves. It also is known that warm thermal contact is effective at vasodilation. It also is believed that vibrational and thermal vasodilation is more effective when applied generally between the pain source or an initiation site and the brain, and more specifically close to the nerve plexi where the various nerve types (pain, temperature and motion) converge in the body, generally at or proximal to a joint.

A thermal element, is cooled or heated, as necessary. For example, if the thermal element is a metal ingot or low freezing point gel, the thermal element is placed in a refrigerator, freezer, or other cold site. Alternatively, if the thermal element is a high specific-heat capacity material like a grain sewn within an insulated fabric it may be microwaved before use to heat it. When the thermal element is of a satisfactory temperature, the thermal element is placed within or adjacent to the casing. The thermal element may be placed within the thermal element pocket, within an attachment element (50) such as an elastic band attached to the casing so that the thermal element is interposed between the elastic band and the proximal side (30) of the device, or within an attachment element (50) such as a clip located on the proximal side of the device as shown in FIGS. 9 A-C and E. The device is contacted to the surface, such as the surface of skin of a subject, at the desired location, depending on the method employed for the desired treatment. In the example shown in FIG. 1, where a site of injection is proximal to the subject's wrist, the device is contacted between the injection site and the subject's brain, and more specifically in the illustrative example shown in FIG. 1, is placed between the initiation site and the subject's elbow and proximal to the nerve plexi proximal to the elbow. In other methods, the device may contact the initiation site directly and not be adjacent to it, as described for certain disclosed methods.

The application area of the device, with the thermal element interposed therebetween, is applied to the selected area of the subject such that the application area, comprising the thermal area and the vibrational area, contact the subject's skin. The thermal element may be contacted with the surface for a time period, without vibration, for example, to allow the thermal element to act upon the subject for a suitable time period so as to initiate thermal effects, for example, vasodilation or vasoconstriction. Alternatively, concurrently with application of the thermal element to achieve thermal effects, the vibrational source is actuated, for example, by pressing the switch, and starting the vibrational source, and vibrations are transferred through the application area (and through the thermal element if present) to the contacted surface. The vibrational source also is allowed to act upon the subject for a suitable time period so as to initiate the desired effect depending on the method of application. After thermal and vibrational effects are initiated, a treatment may occur to the subject or the vibrational and thermal effects may be continued until pain or itching sensations are no longer perceived by the subject.

Once the desired treatment is completed, vessel diameters have been effected, or the sensations are no longer perceived by the subject, the entire device can be removed from contacting the surface, and/or only the thermal element can be removed and the device continues to provide vibration to the surface, or the thermal element may remain in place on the surface and the vibrational source may be turned off. In one illustrative method, the device is left in contact with the subject for a period of between 0 and 60 seconds, or for one or more minutes, to continue to reduce any pain associated with the site.

Figure 6:
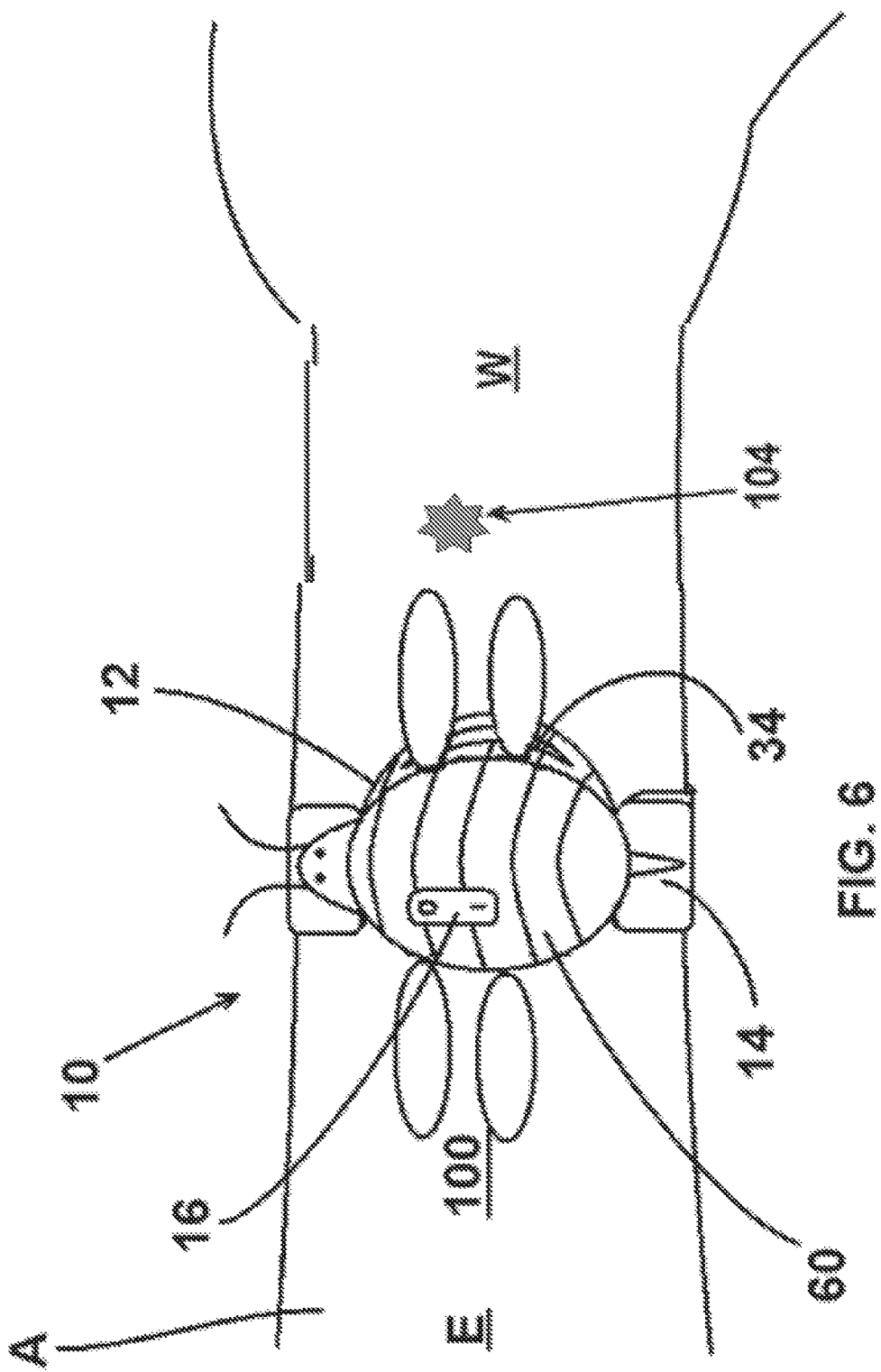
FIG. 6 is a perspective view of an embodiment of the invention having an ornamental cover (60) or a decorated casing (12). The device is depicted in the same use as FIG. 1 with the addition of an ornamental cover (60) or a decorated casing (12) for the purpose of distracting the subject, preferably a child.

Referring now to FIG. 6, alternative embodiments include casings having interesting or distracting shapes or ornamental covers (60) over the casing. Distraction may help reduce pain, especially in children. For example, the casing could be a material in the shape of a bumble bee, as illustrated in FIG. 6, or dinosaur. When the device is applied to a child, the distracting shape both can lessen the fear a child may have to device medical procedure and help to decrease the subsequent pain or unpleasant sensations of the child.

Referring to FIG. 7, a proximal view of a device 10 of the present invention comprising a thermal element 28 (shown as transparent so as to view the proximal side 30 of the device 10). An attachment element 50 (an elastic band) is shown holding the thermal element 28 to the application area 22 of the proximal side 30 of the casing 12 of the device 10.

Figure 8:
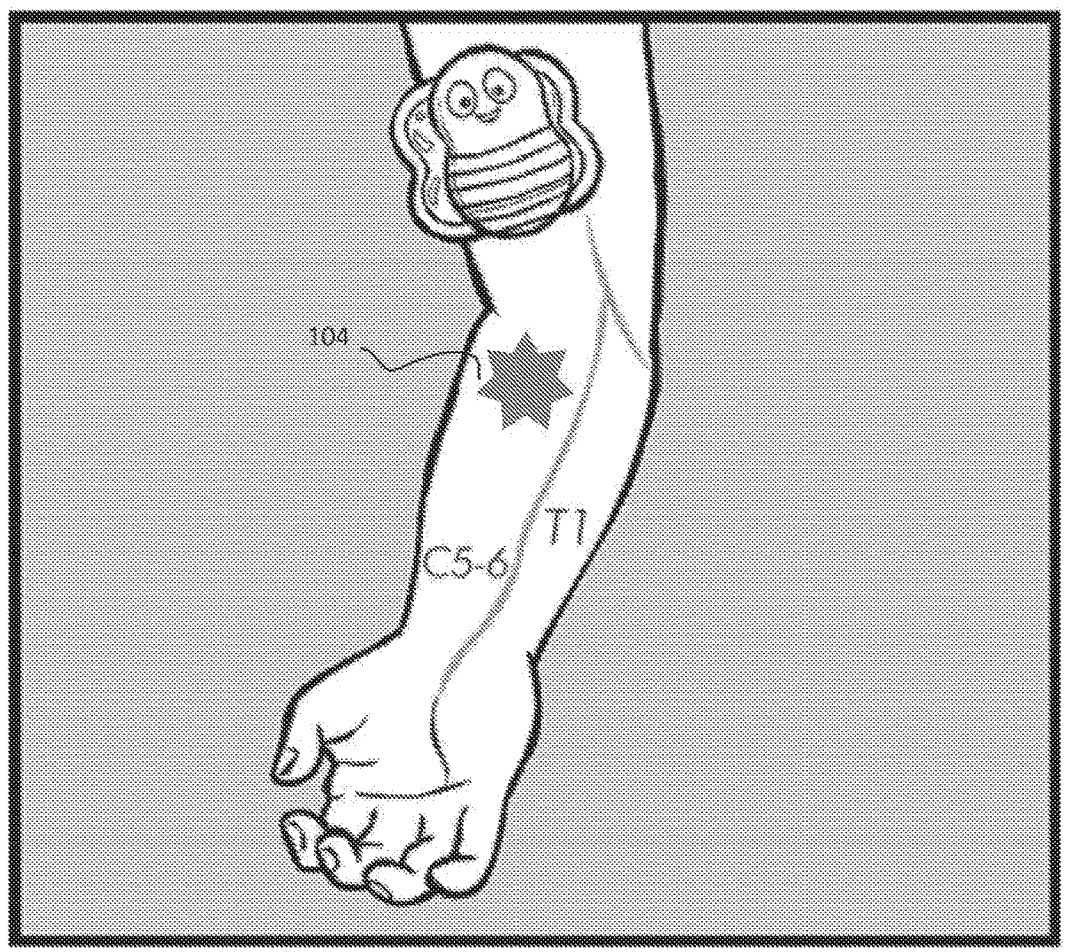
FIG. 8 is a drawing of an exemplary vibratory device of the present invention wherein the device is placed between the initiation site (104) of pain, burning, itching, or injury and the spinal cord.

FIG. 8 shows the placement of a device of the present invention 10 on the arm of a human in a location between an initiation site 104 and the brain/spinal cord of the human.

FIG. 9 A-E shows a drawing of an exemplary device of the present invention having a shaped casing. 9A shows the front or anterior end (31) of the device (10) and its power switch (16), B shows the posterior or rear end (33) of the device (10) with its site indicator (52), and 9C shows the back or proximal side (30) of the device, that is contacts, or is placed proximally or adjacent to, the surface, having a clip (50) for holding a thermal element (not shown) in place. The distal side (30) may be flat or planar in shape, or may be curved, as desired. D shows a front or distal side (37) of the device (10), and E shows a side view (35*a* or 35*b*) of the vibratory device (10) where the attachment element (50) a clip, slightly protrudes from the posterior (lower) (33) proximal end and the on/off switch element (16) is shown at the anterior (upper) end (31). The site indicator (52) provides a guide to the user for placing the device. In methods where applicable, the device is placed so that the indicator is directly at the site of injection, pain, treatment or itching sensation. 9C shows the proximal side 30 of the device 10. For example, the entire proximal side may be the application area 22 and the entire proximal side (30) substantially contacts the surface contacted and the proximal side (30) comprises the application area 22 through which vibration is transferred to the surface. In an aspect, only a portion of the proximal side may be the application area. Also shown is attachment element, 52, which is a clip. The indicator 50 is also shown. FIG. 9D shows the distal side 37 of the device which may be curved in a shaped manner to fit comfortably in a hand when gripped. The lateral sides 35 A and 35*b* are shown as indented in a generally midline position. Other shapes are contemplated by the invention and the indentions may or may not provide a functional or a decorative aspect to the invention. FIG. 9E shows a lateral side 35*a/b* view of the device 10. At the anterior end 31 the switch 16 is visible. The attachment element (clip) 50 is visible on the proximal side 30. The shape of the distal side (37) may be any desired shape, and may be in some embodiments flat or planar, or may be curved, either convex or concave in shape.

Thus, in one of its simplest forms, the invention is a device for providing vibration and/or thermal treatment to a surface, comprising a casing comprising an application area, wherein at least a portion of the application area is shaped to substantially contact a surface, such as a subject's skin, a vibrational source contained within the casing, with said vibrational source capable of producing vibration that is transfer through the casing to at least the surface, and optionally comprising a thermal element capable of transmitting heat or cold. The application area is constructed to allow the transmission of vibration from the vibrational source to the surface, such as a subject's skin, and by the interpositioning of a thermal source between the application area and the surface, providing thermal effects to the surface. The vibration or combination of the vibration and transmission of cold or heat from the thermal element produces vibrational and thermal effects on the subject.

The invention further comprises the use of a removable thermal element. For example, the casing may comprise a flat hook on which a thermal pack could be attached while still transmitting vibrational energy if the pack were soft.

The invention further comprises a vibrational unit with a power source capable of being attached via an adhesive dressing (e.g. tegaderm) or attached to the skin in an array of vibrational units.

The present invention may comprise a kit comprising a vibratory device of the present invention, a thermal element and an instructions for use of the device.

As used herein, subject means a human or animal, and includes any living animal on the planet Earth.

The above detailed description of the preferred embodiments, and the examples, are for illustrative purposes only and are not intended to limit the scope and spirit of the invention, and its equivalents, as defined by the claims. One skilled in the art will recognize that many variations can be made to the invention disclosed in this specification without departing from the scope and spirit of the invention.

REFERENCES

Baxter A L, Leong T, Mathew B. External Thermomechanical Stimulation versus Vapocoolant for Adult Venipuncture Pain: Pilot Data on a Novel Device. Clin J Pain 2009; 25(8):705-710.

Baxter A L, Cohen L L, Lawson M L, Von Baeyer C L. A Randomized Clinical Trial of a Novel Vibrating Tourniquet to Decrease Pediatric Venipuncture Pain. Pediatr Emerg Care 2011; 27(12): 1151-6.

Bovenzi M, Lindsell C J, Griffin M J. Duration of acute exposures to vibration and finger circulation. Scand J Work Environ Health 1998; 24(2): 130-7.

Figueroa A, Gil R, Sanchez-Gonzalez M A. Whole-body vibration attenuates the increase in leg arterial stiffness and aortic systolic blood pressure during post-exercise muscle ischemia. Eur J Appl Physiol 2011; 111(7):1261-8.

Figueroa A, Gil R, Wong A, Hooshmand S, Park S Y, Vicil F, et al. Whole-body vibration training reduces arterial stiffness, blood pressure and sympathovagal balance in young overweight-obese women. Hypertens Res 2012.

Freeman A W, Johnson K O. A model accounting for effects of vibratory amplitude on responses of cutaneous mechanoreceptors in macaque monkey. J Physiol 1982; 323:43-64.

Hess H A. A biomedical device to improve pediatric vascular access success. Ped Nurs 2010; 36(5): 259-263.

Inal S, Kelleci M. Buzzy relieves pediatric venipuncture pain during blood specimen collection. MCN Am J Matem Child Nurs 2012; in press.

Skoglund C R. Vasodilatation in human skin induced by low-amplitude high-frequency vibration. Clin Physiol 1989; 9(4):361-72.

Spandorfer P R, Alessandrini E A, Joffe M D, Localio R, Shaw K N. Oral versus intravenous rehydration of moderately dehydrated children: a randomized, controlled trial. Pediatrics 2005; 115(2):295-301.

Taddio A, Soin H K, Schuh S. Koren G, Scolnik D. Liposomal lidocaine to improve procedural success rates and reduce procedural pain among children: a randomized controlled trial. Cmaj 2005:172(13): 1691-5.

Thompson A J, Griffin M J. Effect of the magnitude and frequency of hand-transmitted vibration on finger blood flow during and after exposure to vibration. Int Arch Occup Environ Health 2009; 82(9):1151-62.

What is claimed is:

1. A method for increasing fluid flow in a site of reduced fluid flow in a subject, the method comprising:
   i. contacting a vibratory device at or adjacent to a site of reduced fluid flow, wherein the vibratory device comprises a) a casing comprising an application area, b) a vibrational source contained within the casing, wherein the vibrational source is capable of producing vibration, c) a switch secured to the casing and in operative communication with the vibrational source for selectively activating the vibrational source, and d) a thermal source contained within the casing, wherein the thermal source is capable of being heated or cooled;
   ii. initiating vibration by the device by activating the vibrational source using the switch, and providing a thermal effect simultaneously with vibration; and
   iii. modulating the fluid flow in the site of reduced flow; wherein the application area is configured to transfer vibration from the vibration source to the site's surface.

2. The method of claim 1, wherein the reduced fluid flow is reduced blood flow in tissue at or adjacent to an injured, wounded or burned site, or is reduced fluid flow in a duct, a pulmonary passage, a mammary duct, an artery, vein or capillary.

3. The method of claim 1, wherein the vibration is a single vibration cycle or multiple vibration cycles.

4. The method of claim 1, wherein the vibration per minute is constant or variable.

5. The method of claim 4, wherein the vibration is 6,000 to 15,000 vibrations per minute.

6. The method of claim 4, wherein the vibrations are variable, and the vibrations per minute cycle between 6,000 to 15,000 vibrations per minute.

7. A method for reducing pain or irritating sensation at a site of such sensations in a subject, the method comprising:
   i. contacting a vibratory device at a site of the pain or irritating sensation in a subject, wherein the vibratory device comprises a) a casing comprising an application area, b) a vibrational source contained within the casing, wherein the vibrational source is capable of producing vibration, c) a switch secured to the casing and in operative communication with the vibrational source for selectively activating the vibrational source, and d) a thermal source contained within the casing, wherein the thermal source is capable of being heated or cooled;

ii. providing vibration by the device in an intermittent or continuous vibration, and applying a thermal effect simultaneously with the vibration, and iii. vibrating for a sufficient time to reduce the pain or irritating sensation at the site in a subject;

wherein the application area is configured to transfer vibration from the vibration source to the site's surface.

8. The method of claim 7, wherein the pain or irritating sensation is injection site pain, burning, itching, neuropathic pain, nerve pain, or phantom pain.

9. The method of claim 7, wherein the vibration is a single vibration cycle or multiple vibration cycles.

10. The method of claim 7, wherein the vibration per minute is constant.

11. The method of claim 10, wherein the vibration is 6,000 to 15,000 vibrations per minute.

12. The method of claim 7, wherein the vibration is variable.

13. The method of claim 12, wherein the variable vibrations per minute cycle between 6,000 to 15,000 vibrations per minute.

14. A method for enhancing fluid flow at a site in a subject, the method comprising i. contacting a vibratory device at a site in a subject, wherein the vibratory device comprises a) a casing comprising an application area, b) a vibrational source contained within the casing, wherein the vibrational source is capable of producing vibration, c) a switch secured to the casing and in operative communication with the vibrational source for selectively activating the vibrational source, and d) a thermal source contained within the casing, wherein the thermal source is capable of being heated or cooled;

ii. providing, by activating the vibrational source using the switch, vibration by the device in an intermittent or continuous vibration, and applying a thermal effect simultaneously with the vibration, and iii. vibrating for a sufficient time to enhance fluid flow at the site in the subject;

wherein the application area is configured to transfer vibration from the vibration source to the site's surface.

15. The method of claim 14, wherein the enhanced fluid flow is at an artery, vein or capillary in the subject.

16. The method of claim 14, wherein the vibration is a single vibration cycle or multiple vibration cycles.

17. The method of claim 14, wherein the vibration per minute is constant.

18. The method of claim 17, wherein the vibration is 6,000 to 15,000 vibrations per minute.

19. The method of claim 14, wherein the vibration is multiple vibration cycles, and the vibrations per minute cycle between 6,000 to 15,000 vibrations per minute.

* * * * *